United States Patent
Blaauw et al.

(10) Patent No.: US 8,404,647 B2
(45) Date of Patent: Mar. 26, 2013

(54) PEPTIDYLARGININE DEIMINASE (PAD) INHIBITORS

(75) Inventors: Richard Hendrik Blaauw, Nijmeghen (NL); Gerardus Jozef Maria Pruijn, Beuningen (NL); Jozef Maria Hendrik Raats, Nijmegen (NL); Floris Petrus Johannes Theodorus Rutjes, Wijchen (NL); Jan Wouter Drijfhout, Leiden (NL)

(73) Assignees: Chiralix B.V., Nijmegen (NL); Modiquest B.V., Nijmegen (NL); Academisch Ziekenhuis Leiden H.O.D.N. Lumc, Leiden (NL)

( * ) Notice: Subject to any disclaimer, the term of this patent is extended or adjusted under 35 U.S.C. 154(b) by 0 days.

(21) Appl. No.: 12/965,536

(22) Filed: Dec. 10, 2010

(65) Prior Publication Data

US 2011/0142868 A1    Jun. 16, 2011

Related U.S. Application Data

(63) Continuation of application No. PCT/NL2009/050340, filed on Jun. 15, 2009.

(60) Provisional application No. 61/061,754, filed on Jun. 16, 2008.

(30) Foreign Application Priority Data

Jun. 16, 2008 (EP) ..................................... 08158330

(51) Int. Cl.
*A61K 38/10* (2006.01)
*A61K 38/16* (2006.01)
*A61K 38/08* (2006.01)

(52) U.S. Cl. ...................... 514/21.4; 514/21.5; 514/21.6

(58) Field of Classification Search ........................ None
See application file for complete search history.

(56) References Cited

U.S. PATENT DOCUMENTS

| 6,284,735 | B1 * | 9/2001 | Girten et al. | 514/9.8 |
| 2005/0159334 | A1 | 7/2005 | Gluck et al. | |
| 2006/0057668 | A1 * | 3/2006 | Yoshida et al. | 435/69.1 |

FOREIGN PATENT DOCUMENTS

| CA | 2421321 A1 | 9/2004 |
| EP | 1717224 A | 11/2006 |
| WO | WO 99/14232 * | 9/1998 |
| WO | WO 98/53069 * | 11/1998 |
| WO | WO01/ 46222 A | 6/2001 |
| WO | WO2007/076302 A | 7/2007 |

OTHER PUBLICATIONS

Hunter. Synthetic Peptide Substrates for a Tyrosine Protein Kinase. The Journal of Biological Chemistry. 1982. vol. 257, No. 9, pp. 4843-4848.*

Ongena M., et al.: Unusual traits of the pyoverdin-mediated iron acquisition system in pseudomas putida strain BTP1, Biometals, vol. 15, 2002, pates 1-13.

Girbal-Neuhauser, E., et al., The epitopes targeted by the rheumatoid arthritis-associated antifilaggrin autoantibodies are posttranslationally geneneated on various sites of (Pro) filaggrin b deimidation of arginine residures, Jouranl of Immunology, American Association of Immunogists, US, vol. 162, No. 1, Jan. 1, 1999, pp. 585-5694.

Hidaka et al., Methylation of the guanidino group of arginine residues prevents citrullination by peptidylargine deiminase IV, Febs Letters, Elsevier, Amsterdam, NL, vol. 579, No. 19, August 1, 2005, pp. 4008-4092.

Algeciras Mabel E., et al., Targeting optic nerve citrullination in glaucoma: a role for protein-arinine deiminase 2 (PAD2) inhibitors, Drugs of the Future, Prous Science, ES, vol. 32, No. 11, Nov. 1, 2007, pp. 999-1005.

Chang, X, et al., The inhibition of antithrombin by peptidylargine deiminase 4 may contribute to pathogenesis of rheumatoid arthritis, Rheumatology, vol. 44, No. 3, Nov. 23, 2004, pp. 293-298.

* cited by examiner

*Primary Examiner* — Marcela M Cordero Garcia

(74) *Attorney, Agent, or Firm* — Sunstein Kann Murphy & Timbers LLP

(57) ABSTRACT

The invention relates to PAD inhibitors that are suitable to be used as a medicament against an autoimmune disease such as RA.

28 Claims, 7 Drawing Sheets

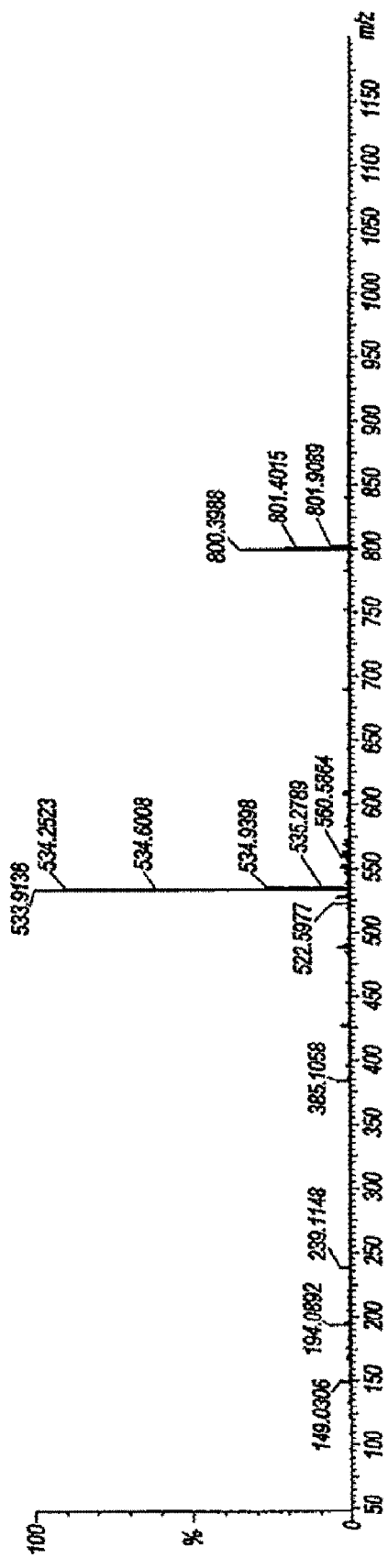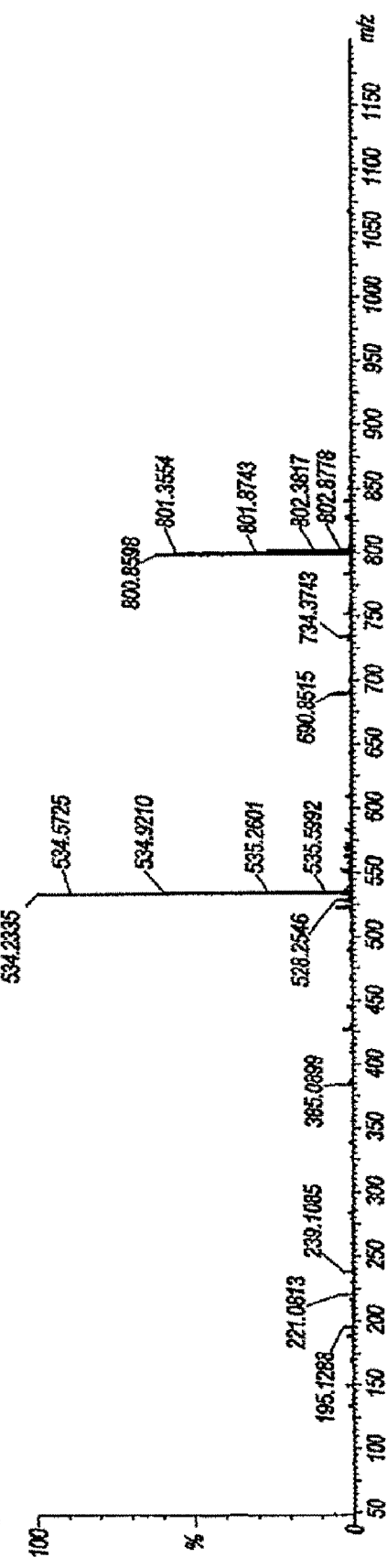

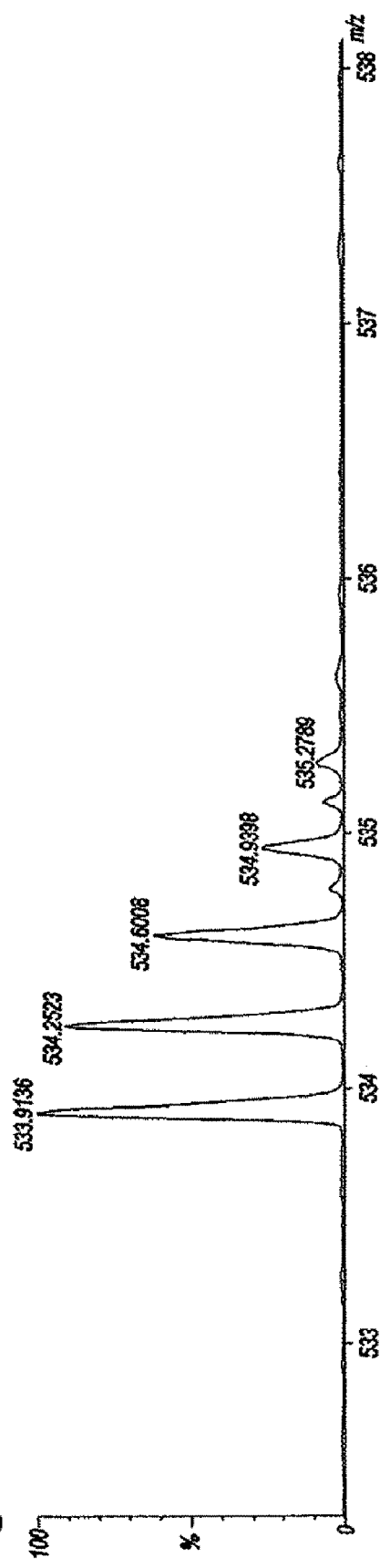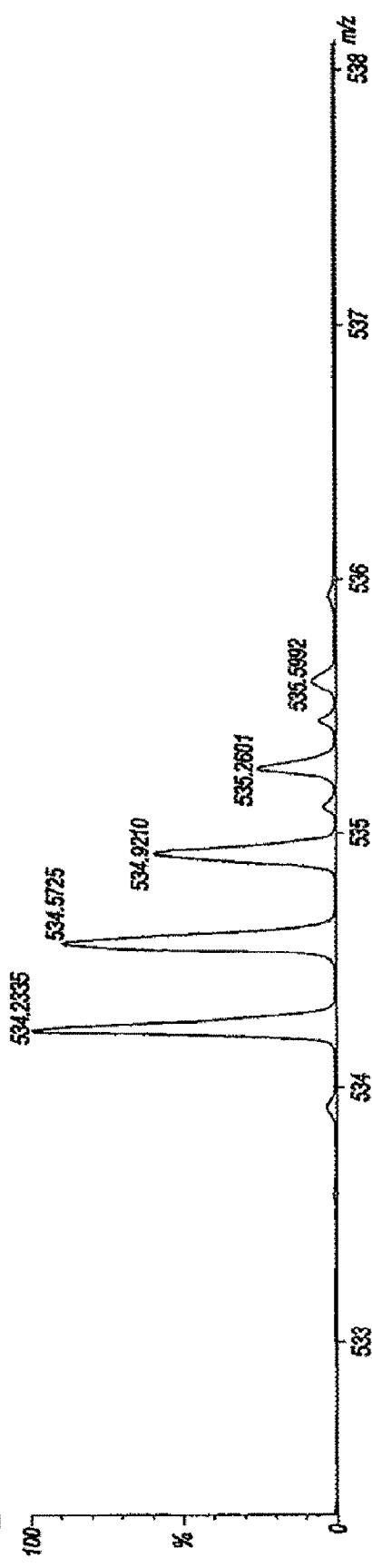
Fig 5b.1
Fig 5b.2

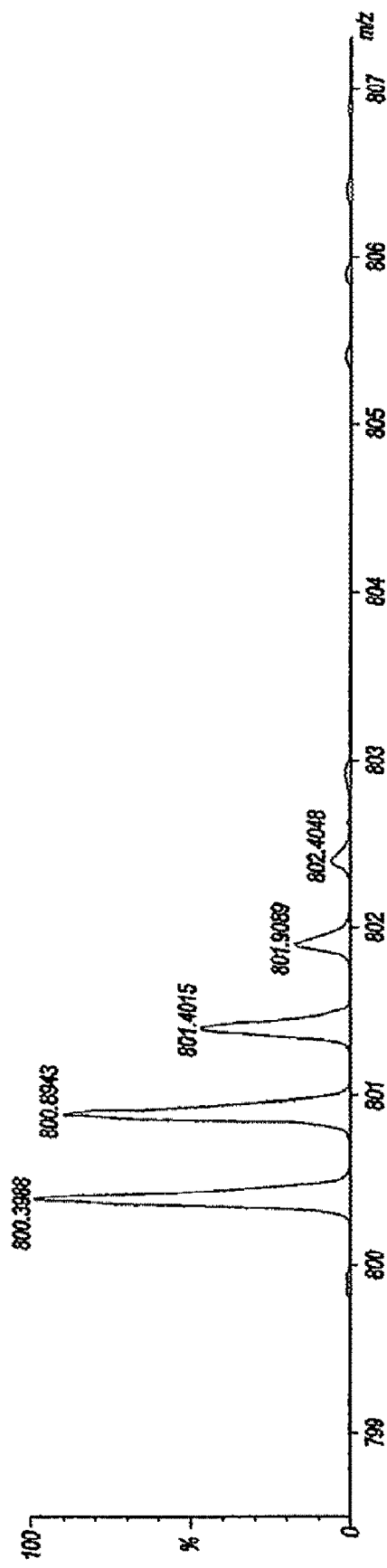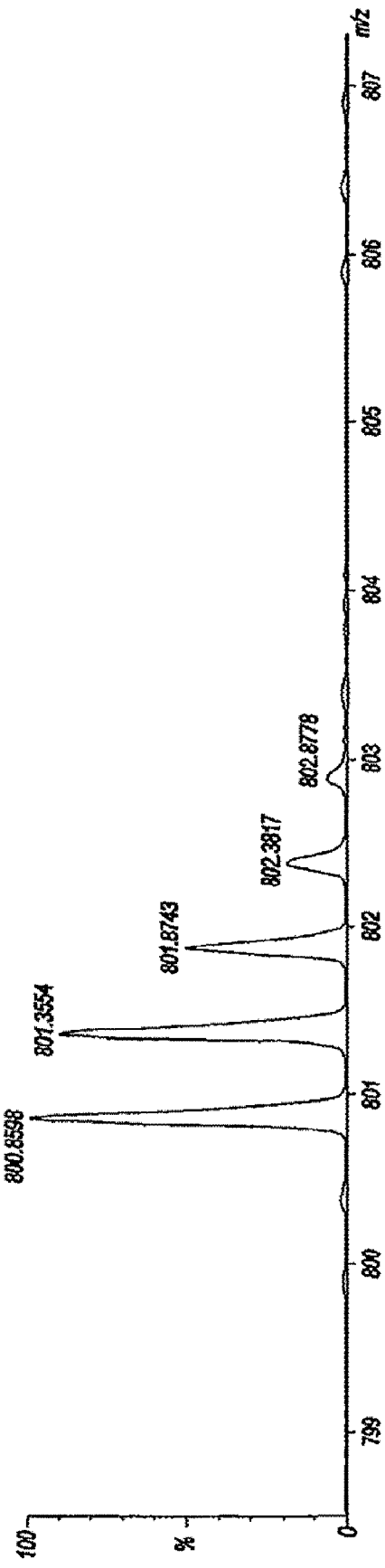

PEPTIDYLARGININE DEIMINASE (PAD) INHIBITORS

RELATED APPLICATIONS

This application is a continuation patent application which claims priority to International Application No.: PCT/NL2009/050340 filed On Jun. 15, 2009, which claims priority to European Patent Application No. 08158330.4, filed on Jun. 16, 2008, which claims the benefit of U.S. Provisional Application No. 61/061,754, filed on Jun. 16, 2008, the entirety of each are herein incorporated by reference.

SEQUENCE LISTING

The instant application contains a Sequence Listing which has been submitted in ASCII format via EFS-Web and is hereby incorporated by reference in its entirety. Said ASCII copy, created on Sept. 12, 2012, is named 87759CON306683_Sequence_Listing_ST25.txt and is 33,870 bytes in size.

FIELD OF THE INVENTION

The current invention relates to the field of medicine, in particular to the prevention and treatment of autoimmune diseases and most specifically to rheumatoid arthritis (RA). The current invention also relates to the field of enzymology. The invention pertains to a method to develop enzyme inhibitors and discloses potent inhibitors of the peptidylarginine deiminase (EC 3.5.3.15) enzyme. These PAD inhibitors may be used for the preparation of medicaments for the treatment of autoimmune diseases, in particular for the treatment of RA, psoriasis and multiple sclerosis (MS).

BACKGROUND OF THE INVENTION

RA is a common autoimmune disease prevalent in about 1% of the world-wide population. It is multifactorial in origin and characterized by the inflammation of the synovial membrane of joints, resulting in swelling of the joints and pain. The inflammatory process frequently leads to cartilage destruction and irreversible bone erosion.

Anti-CCP autoantibodies play an important role in the onset and perpetuation of RA. First, anti-CCP antibodies have been demonstrated to be highly specific for RA. The results of several studies show that each individual that is seropositive for these antibodies either already has RA or will develop this disease in the future. The presence of anti-CCP antibodies (especially when high titers are present) is predictive of erosive disease outcome {Nijenhuis et al., 2004}. Finally, it has been demonstrated that anti-CCP antibodies are produced locally at the site of inflammation. The proportion of anti-CCP antibodies with respect to total IgG found in synovial material from RA patients appeared to be significantly higher than that in serum of the same patients {Masson-Bessière et al, 2000, Reparon-Schuijt et al, 2001}. The presence of anti-CCP producing plasma cells in the synovium is indicative of an antigen-driven maturation of CCP-specific B cells at the site of inflammation. Support for a role of anti-CCP antibodies in the generation of arthritis comes from studies in FcγRIIB knock-out mice. Immunoglobulins from plasma or serum from patients with active RA were demonstrated to induce inflammation and histological lesions in these mice {Petkova et al, 2006}. In a collagen-induced arthritis model, antibodies against citrullinated proteins were reported to enhance tissue injury, substantiating the direct role of these antibodies in the pathogenesis of autoimmune arthritis {Kuhn et al, 2006}. In a recent paper Hill and colleagues report that citrullinated fibrinogen is able to induce arthritis, characterized by synovial hyperplasia followed by ankylosis, in DR4-IE transgenic mice. T-cell epitope scanning and antibody microarray analysis identified a unique pattern of citrulline-specific reactivity that was not found in DR4-IE transgenic mice immunized with unmodified fibrinogen or in wild-type C57BL/6 mice immunized with citrullinated fibrinogen. These observations directly implicate citrullinated fibrinogen as arthritogenic in the context of RA-associated MHC class II molecules {Hill et al, 2008}.

In agreement with this antigen-driven mechanism, the presence of citrullinated proteins in the inflamed RA synovium has been demonstrated. Citrullinated forms of the α- and β-chains of fibrin have been reported to occur not only in the synovium of RA patients {Masson-Bessière et al, 2001}. The molecular characterization of the Sa antigen identified Sa as citrullinated vimentin. The Sa antigen, which is specifically targeted by RA autoantibodies, has been reported to be present in the inflamed synovium. Calcium influx in monocyte-derived macrophages, which are abundantly present in the inflamed synovium, leads to citrullination of vimentin, and the fact that vimentin can be secreted by macrophages in response to pro-inflammatory signaling pathways is consistent with a role for citrullinated vimentin in the development of RA {Vossenaar and van Venrooij, 2004}. In addition to fibrin and vimentin, other citrullinated autoantigens may be produced in an inflamed joint. Using a proteomic approach 13 autoantigenic citrullinated proteins, including fibrinogen, were identified in synovial tissue of an RA patient {Matsuo et al, 2006}. The citrullinating enzyme PAD4 (see below) has been reported to be activated in dying granulocytes, and this leads to citrullination of nuclear proteins {Nakashima et al., 2002}. It is likely that in the inflamed synovium apoptotic granulocytes are not cleared properly, a phenomenon previously observed in systemic lupus erythematosus patients {Ren et al, 2003}, and as a result the citrullinated proteins might become exposed to the immune system.

Citrullination is the posttranslational conversion of arginine residues to citrulline residues, which is catalyzed by peptidylarginine deiminase (PAD). Peptidylarginine deiminase (PAD; EC 3.5.3.15) enzymes catalyse the conversion of arginine residues to citrulline residues in proteins. No tRNA exists for citrulline, the presence of citrulline residues in proteins is exclusively the result of post-translational modification. In mammals (humans, mice and rats) five PAD isotypes (PAD1-PAD6; 'PAD4' and 'PAD5' are used for the same isotype), each encoded by a distinct gene, have been identified {Vossenaar et al, 2003b}. All these enzymes rely strongly on the presence of $Ca^{2+}$ for activity and are unable to convert free L-arginine into free L-citrulline. Free L-arginine can be converted to free L-citrulline by nitric oxide synthase (EC 1.14.13.39) in eukaryotes or by arginine deiminase (EC 3.5.3.6) in bacteria. These enzymes are not $Ca^{2+}$ dependent.

The most pronounced difference between the highly homologous PAD enzymes is their tissue-specific expression. In epidermis PAD1 (synonyms: PAD I, PAD type I) is involved in the citrullination of keratin filaments during the final stages of keratinocyte differentiation, which is important for the reorganization of the cornified envelope. Another site of citrullination in the epidermis is the hair follicle, which contains PAD3 (synonyms PAD III, PAD type III) and its natural substrate trichohyalin (THH). THH is a major structural protein of the inner root sheath cells and the medulla layer of the hair follicle and, to a lesser extent, of other specialized epithelia. The most recently identified PAD isotype, PAD6 (synonym: ePAD), was found in cytoplasmic sheets of mouse oocytes, which play an important role in early embryogenesis. The expression of its human orthologue was found to be restricted to ovary, testis and peripheral blood leukocytes {Chavanas et al., 2004}. Originally, this PAD isotype was designated ePAD, but based upon the systematic numbering of other PADs, this isotype was renamed PAD6 {Vossenaar et al., 2003b}. The most widely expressed isotype, PAD2 (synonyms PAD II, PAD type II, PAD-H19), is present in many different tissues, like skeletal muscle, brain, spleen, secretory glands and macrophages. Despite this broad expression pattern, only myelin basic protein (MBP) and vimentin have been identified as natural substrates. MS patients develop an autoimmune response against MBP. MBP is an abundant protein of the myelin sheath, and its citrullination occurs during development of the central nervous system. Citrullination of vimentin was observed during calcium-ionophore induced apoptosis of human and mouse macrophages and, as described above, citrullinated vimentin was shown to be the target of the RA-specific anti-Sa autoantibodies. In contrast to the PADs discussed above, which are all mainly localized in the cytoplasm of cells, the PAD4 isotype (synonyms: PAD IV, PAD type IV, HL-60 PAD, PAD V, PAD type V, PADI4) is localized in the nucleus. The nuclear localization signal of PAD4 was found in the N-terminal region of the protein. PAD4 is mainly expressed in peripheral blood granulocytes and monocytes. Substrates of PAD4 in the nucleus are histone core proteins (H2A, H3 and H4) and nucleophosmin/B23, a nucleolar protein that functions in ribosome assembly, nucleocytoplasmic transport and centrosome duplication.

Based on these expression profiles, two PAD isotypes, PAD2 and PAD4, are the candidates for the citrullinating enzymes that play a role in protein citrullination associated with the immune response in RA. PAD2 and PAD4 are present in monocytes, macrophages, and granulocytes, cells which are abundantly present in the inflamed synovium {Chapuy-Regaud et al., 2003}.

PADs are normally present in the cytosol or nucleoplasm as inactive enzymes because the local calcium ion concentration is lower than what is required for their activation. During cell death, however, the integrity of the plasma membrane is lost, resulting in an influx of $Ca^{2+}$ from the extracellular space (the extracellular $Ca^{2+}$ concentration is ~$10^{-3}$ M, sufficient for PAD activity) and subsequent activation of intracellular PAD. Alternatively or simultaneously, the activated PAD enzymes may leak out of the dying cells and catalyze the citrullination of extracellular proteins.

A few years ago the crystal structure of the human PAD4 protein was described {Arita et al., 2004}. A comparison of the crystal structures of PAD4 in the presence and absence of calcium ions and of a catalytically inactive mutant with and without bound substrate revealed five $Ca^{2+}$-binding sites and indicated that $Ca^{2+}$-binding induces conformational changes that generate the active site cleft. The structural data confirmed the positioning of a catalytic triad, Cys-His-Glu/Asp, which was previously proposed to represent the core of the catalytic site partly based upon structural information of other arginine-modifying enzymes, in the active site cleft. Based on this conservation pattern and the assumption that the substrate binding mode is similar to that of other arginine-converting enzymes, like dimethylarginine dimethylaminohydrolase and L-arginine deiminase, the catalytic mechanism was proposed {Shirai et al., 2001}. The main players are Cys-645, which mounts the nucleophilic attack on the carbon atom of the guanidinium group of arginine, and His-471, which serves as a general base.

As illustrated above, increasing evidence supports a role for the anti-CCP antibodies and their antigenic targets in the pathophysiology of RA. The role for citrullinated proteins in the etiology of RA is further supported by the citrulline-dependent interaction of citrullinated peptides with RA-associated HLA haplotypes {Hill et al, 2003}. As indicated above, recent data from the same group indicate that arthritis is indeed induced by citrullinated fibrinogen in DR4-IE transgenic mice {Hill et al, 2008}. Taken together, these data indicate that the specific generation of anti-CCP antibodies in RA is mediated at the level of exposure of citrullinated antigens to the immune system and/or the recognition of citrullinated antigens by the immune system. Once anti-CCP antibodies are produced, the formation of immune complexes with citrullinated proteins in the synovia may trigger the progression of the inflammatory process. A role for the anti-CCP antibodies in the pathogenesis of RA is supported by the results of B lymphocyte depletion experiments in patients with RA {Cambridge et al., 2003}.

PAD enzymes and their products, citrullinated proteins, are known to play a role in several other human diseases, in particular autoimmune diseases such as psoriasis, MS and systemic lupus erythematosus.

In psoriasis, keratinocytes proliferate very rapidly and travel from the basal layer to the surface in only about four days. The skin can not shed these cells quickly enough so they accumulate in thick, dry patches, or plaques. In normal keratinocytes, keratin K1 is citrullinated by PAD1 during terminal differentiation. This process causes the keratin filaments to become more compact, which is essential for the normal cornification process of the epidermis. The keratinocytes in the psoriatic hyperproliferative plaques do not contain citrullinated keratin K1 {Ishida-Yamamoto et al., 2000}. It is not clear whether the increased cell proliferation prevents adequate citrullination by PAD or that inactivity of PAD allows hyperproliferation and accumulation of keratinocytes. Although the mechanism is unknown, aberrant citrullination in psoriatic epidermis obviously is related to PAD1.

MS is a chronic inflammatory disorder of the CNS, characterized by autoimmunity mediated destruction of the myelin sheath. The cells of the myelin sheath form a multi-bilayer structure around the axons consisting of lipid-protein complexes in a ratio of about 3:1. Two major proteins, MBP and proteolipid protein, account for 85% of the protein fraction. MBP is a highly cationic protein, capable of forming strong interactions with negatively charged phospholipids such as phosphatidylserine. In approximately 18% of the MBP molecules of healthy adult humans 6 (out of 19) arginines are citrullinated {Wood et al., 1989, Wood et al., 1996}. The remaining MBP molecules do not contain citrulline. In MS patients the proportion of MBP-cit6 is increased to 45% of total MBP. The decreased net positive charge of MBP-cit6 causes partial unfolding of MBP molecules and weakens their interaction with the phospholipids {Boggs et al., 1999, Pritzker et al., 2000}. Although MBP-cit6 is capable of forming lipid complexes more rapidly than non-citrullinated MBP, the complexes that are formed are not as densely packed as those formed with non-citrullinated MBP {Boggs et al, 1999, Beniac et al, 2000}. MBP-cit6 is degraded 4 times more rapidly by cathepsin D than non-citrullinated MBP {Cao et al., 1999}. In a rare case of acute fulminating MS (Marburg type), 80% of the MBP molecules are heavily citrullinated (MBPcit18) {Wood et al., 1996}. The severely unfolded MBP-cit18 is degraded 45 times more rapidly by cathepsin D than normal MBP {Cao et al., 1999}. Clinical trials with paclitaxel, the active component of the anti-cancer drug taxol, are in progress {O'Connor et al., 1999}. Low doses of paclitaxel can inhibit citrullination of MBP by PAD2 in vitro {Pritzker et al., 1998}. Treatment with paclitaxel attenuates clinical symptoms and induces remyelination of damaged sheaths {Moscarello et al., 2002}, underlining the possible importance of PAD as a candidate factor in demyelinating disease {Moscarello et al., 2002 2x}.

DETAILED DESCRIPTION OF THE INVENTION

One potential target for intervention in autoimmune diseases associated with (alterations in the level of) citrullinated proteins is PAD. Blocking the production of citrullinated proteins at the site of inflammation, for instance in the RA inflamed synovium, will impede the formation of immune complexes and thus is expected to inhibit the progression of the inflammatory process in the affected joint. Because there is no obvious physiological role for citrullinated proteins in the synovium, interfering with their production is not expected to lead to severe side-effects.

Thus, therapeutic intervention aimed at the specific inhibition of PAD activity, preferably at the site of the unwanted autoimmune reaction, for instance in the inflamed synovium, will be highly specific for the joint destructing processes in RA patients.

Similarly to RA, also in patients suffering from MS excessive or aberrant citrullination of myelin basic protein (MBP) may be prevented by the administration of PAD inhibitors, which will result in more densely packed lipid complexes in the myelin sheets, a better folding of MBP and in making MBP less susceptible to degradation by cathepsin D. Currently low doses of paclitaxel are used to inhibit citrullination of MBP by PAD2 in clinical trials. Treatment with paclitaxel attenuates clinical symptoms and induces remyelination of damaged sheaths {Moscarello et al., 2002}. Paclitaxel however is a highly toxic drug with many adverse side effects, even at low dose. Paclitaxel and taxol compounds are not specific PAD inhibitory molecules.

Currently no specific PAD inhibitors have been disclosed that are suitable for treatment of other autoimmune disorders, such as RA, MS, SLE or psoriasis. It is an object of the current invention to provide molecules capable of reversible or preferably irreversible inhibition of the PAD enzyme, in particular human PAD2 and PAD4 enzymes.

Benzoyl-L-arginine ethyl ester (BAEE) has been extensively used as a substrate to determine PAD activity. A related compound, benzoyl-L-arginine amide, was used as a substrate to determine the crystal structure of the PAD4-substrate complex. This suggested that, although PADs do not convert free L-arginine to L-citrulline, compounds chemically related to BAEE might fit into the active site cleft and compete for binding of substrate molecules. Of particular interest in this respect is the cysteine that is part of the catalytic triad, and is proposed to play an essential role in nucleophilic catalysis. By stabilizing the tetrahedral adduct in the catalytic cleft, the formation of citrullinated product may be prevented. Therefore, the current invention provides PAD inhibitors that are based on covalent modification of the active site cysteine to successfully achieve inhibition, preferably at low doses of the inhibitor. The inhibitors disclosed may inhibit PAD in a reversible manner, but preferably will irreversibly and/or covalently bind to the PAD enzyme, most preferably to the active site catalytic cysteine residue.

Compound

In a first aspect, the current invention provides a new molecule or compound capable of inhibiting a peptidylarginine deiminase (PAD). Inhibition of PAD is herein defined as the capability of a compound to inhibit the activity of a PAD in vitro using the assay as provided in any one of examples 4, 5, 6, and/or 7. The term "inhibiting" is art-recognized and refers to down regulation or suppression of a PAD activity (PAD2 and/or PAD4 activities) either the two in combination or apart. This inhibition preferably means an inhibition of at least 5% of the initial activity of said enzyme without said compound using a minimal concentration of preferably at least 0.0000001 mM or 0.000001, 0.00001, 0.0001, 0.001, 0.01, 0.1, 0.5, 1, 2, 5 or 10 mM of said compound. The activity of a PAD enzyme being measured as described in Example 6. More preferably, an inhibition means an inhibition of at least 10%, even more preferably at least 20%, at least 30%, at least 40%, at least 50%, at least 70%, at least 90%, at least 95% or more. Most preferably, no PAD2 and/or no PAD4 activity is detectable. Any compound of the invention as defined herein, which is able to inhibit the activity of a PAD as defined herein, is expected to be functional as a medicament to be used to prevent, treat and/or delay an autoimmune disorder such as RA.

A compound of the invention is preferably capable of inhibiting the activity of a PAD, more preferably of PAD2 and/or PAD4. This compound preferably comprises a peptide part and an electrophilic group, preferably a thiol-reactive electrophilic group carried by an amino acid Ω wherein
 (a) the peptide comprises at least about 5 amino acids and no more than about 20 amino acids,
 (b) the peptide part comprises at least one of the motifs (b1), (b2), (b3) or (b4):
(b1) G/S/T-D/S-Ω-D/G/S-G/S
(b2) H/K/F/L/W-S/D/H-ΩD/E-H/Y/F/W
(b3) Y/A/K/H/L-F/Y/H-ΩN/G/H/Y-K/A/F
(b4) Y-D/S-ΩD/G/S-G/S
in which Ω represents an amino acid carrying an electrophilic group, preferably a thiol-reactive electrophilic group.
 (c) optionally the N-terminus and/or C-terminus of the peptide sequence are modified.

The peptide part is represented by a peptide sequence. Peptide sequences encompassed by the present invention therefore may consist of or comprise a sequence with a (b1), (b2), (b3) and/or a (b4) motif as defined above. A peptide sequence encompassed by the present invention may therefore be a juxtaposition of two or three or more of the (b1), (b2), (b3) and (b4) motifs. However, preferred peptide sequences comprise or consist of a (b1) or (b2) or (b3) or (b4) motif, even more preferably of a single (b1) or (b2) or (b3) or (b4) motif. Even more preferred peptide sequences consist of or comprise a (b1) or a (b2) or a (b4) motif.

A preferred compound comprise or consists of SEQ ID NO:12-21, 107-143, preferably 20-21, 120, 122, 127-143, more preferably 20, 21, 127, 128, 136-143, even more preferably 138, 141, 142, 143.

Even more preferred peptide sequences comprising or consisting of a (b1) motif are found in example 1: see all peptide sequences of table 2 except the one of L1 which is used as a control (SEQ ID NO: 1-10 and L1 being SEQ ID NO: 11). In each peptide sequence of the table to obtain the corresponding inhibitor of the invention as defined above, the R should be replaced by Ω. Therefore, preferred peptide sequences comprise or consist of SEQ ID NO: 1-10, wherein R is replaced by Ω. Preferred inhibitors are further found in example 1 (SEQ ID NO: 12-20). Preferred inhibitors therefore comprise or consist of SEQ ID NO 12-20, SEQ ID NO:126, 127, 142. A more preferred inhibitor comprises or consists of SEQ ID NO:20, 127, 142. An even more preferred inhibitor comprises or consists of SEQ ID NO:20 wherein the C-terminus has been modified by addition of an amide. Most preferred inhibitor comprises or consists of SEQ ID NO:142.

Preferred peptide sequences comprising or consisting of a (b2) motif are identified in table 5 and are expected to form a compound that will specifically inhibit at least PAD4: see all peptide sequences of table 5 (SEQ ID NO: 47-71). In each peptide sequence of the table to obtain the corresponding inhibitor of the invention as defined above, the R should be replaced by Ω. Therefore, preferred peptide sequences comprise or consist of SEQ ID NO: 47-71, wherein R is replaced by Ω. Preferred inhibitors comprise or consist of SEQ ID NO 107-125, 129-141. More preferred inhibitors comprise or consist of SEQ ID NO:120, 122, 129-141. Even more preferred inhibitors comprise or consist of SEQ ID NO:136, 137, 138, 139, 140. Most preferred inhibitors comprise or consist of SEQ ID NO:138.

Preferred peptide sequences comprising or consisting of a (b3) motif are identified in table 9 and are expected to form a compound that will specifically inhibit at least PAD2: see all peptide sequences of table 9 except the one of L1 which is used as a control (SEQ ID NO: 92-106 and SEQ ID NO:11 as control L1). In each peptide sequence of the table to obtain the corresponding inhibitor of the invention as defined above, the R should be replaced by Ω. Therefore, preferred peptide sequences comprise or consist of SEQ ID NO: 92-106, wherein R is replaced by Ω.

Preferred peptide sequences identified in table 10 (selected from the ones already identified in tables 5 and 9) are expected to form a compound that will specifically inhibit PAD2 and PAD4: see all peptide sequences of tables 10 except the ones of L1 and L2 which are used as a control. In each peptide sequence of the table to obtain the corresponding inhibitor of the invention as defined above, the R should be replaced by Ω.

Preferred inhibitors comprising a peptide part, said peptide part comprising or consisting of a (b4) motif and being represented by a sequence comprising or consisting of SEQ ID NO:21, 128, 143. A more preferred inhibitor is being represented by a sequence comprising or consisting of SEQ ID NO:143. An even more preferred inhibitor comprises or consists of SEQ ID NO:21 wherein the C-terminus has been modified by addition of an amide. This inhibitor is preferred since it has been shown to exhibit significant inhibitory activities in an in vivo animal model (see example 10).

Preferred compounds of the invention have in their (b1) motif two D residues. Corresponding peptide sequences consist of or comprise G/S/T-D-Ω-D-G/S.

Other preferred compounds of the invention have in their (b2) motif two D residues. Corresponding peptide sequences consist of or comprise H/K/F/L/W-D-Ω-D-H/Y/F/W.

Even more preferred compounds are those wherein the peptide sequence is as identified in any one of tables 4, 5, 9 or 10 (see all peptide sequences of these tables except the one of L1 or L2 which are used as a control. In each peptide sequence of the table to obtain the corresponding inhibitor of the invention as defined above, the R should be replaced by Ω). Even more preferred compounds are those wherein the compound is as identified in any one of tables 11, 12 or 15 (except the one derived from L2 which is used as a control). Inhibitors of table 15 are represented by SEQ ID NO: 107-111. Preferred inhibitors comprise or consist of SEQ ID NO: 107-111.

Each of these compounds has been unambiguously characterized as being a PAD2 and/or PAD4 inhibitor.

A compound according to the invention comprise a peptide part of at least about 5 and no more than about 35, preferably no more than about, 25, 20, 15, 10, 9, 8, 7 amino acids, is capable of interacting with a PAD enzyme, and may have an affinity ($K_m$) between 1 nM and 1 mM, preferably between 1 nM to 100 μM, preferably between 1 nM to 10 μM. In the invention, we unambiguously demonstrated that a length of 7 amino acids was sufficient to confer specificity to the compound (only a PAD enzyme, preferably a PAD2 and/or PAD4, will be inhibited and no other enzyme class) and are powerful PAD2 and/or PAD4 inhibitors. Such a length is quite attractive since such compounds are easy to be chemically synthesized. Accordingly, a compound according to the invention comprise a peptide part of at least 5 and no more than 35, preferably no more than 34, 33, 32, 31, 30, 29, 28, 27, 26, 25, 24, 23, 22, 21, 20, 19, 18, 17, 16, 15, 14, 13, 12, 11, 10, 9, 8, 7 amino acids and is capable of interacting with a PAD enzyme as defined herein. Preferred compounds comprises a peptide part, said peptide part comprising a length of 7 amino acids. Herein peptide sequences are described that are read from left to right, with the amino (N-) terminus located at the left side and the carboxy (C-) terminus located at the right side.

Electrophilic Group

A compound according to the invention preferably comprises an electrophilic group, more preferably a thiol reactive electrophilic group, optionally connected via a spacer moiety to the peptide part. An electrophilic group is a moiety with low electron density (also called electrophile) that is able to react with another moiety having high electron density (also called nucleophile). In this context, a moiety having a low electron density may mean that this moiety has a lower electron density than the moiety having a high electron density. Therefore, a moiety with a high electron density may mean that this is a moiety with a higher electron density than the moiety having a low electron density. The structure and nature of the thiol-reactive electrophilic groups of this application, preferably fluoroamidine or chloroamidine, is such that at room temperature (or at 37° C.) a chemical reaction is possible between the thiol-reactive electrophilic group of the inhibitor and the thiol group in the active center of a PAD enzyme, yielding a covalently coupled enzyme-inhibitor complex.

The electrophilic group or preferably thiol-reactive electrophilic group is preferably carried by an amino acid Ω as identified in the compound of the invention. Ω may be any amino acid. Ω may be a modified amino acid. A compound according to the invention is expected to be capable of interacting with a PAD enzyme, preferably a PAD2 and/or PAD4 and capable of inhibiting their activity, preferably, but not limited to, by interacting with or binding to the thiol moiety of a cysteine residue in the catalytic site (or cleft) on a PAD enzyme. The inhibition has been extensively demonstrated in the examples of the application.

The thiol reactive electrophilic group or electrophilic group or electrophilic trap is connected to the peptide part of the molecule, optionally via a spacer group or moiety, and may be any thiol reactive, electrohilic group known in the art which may be easily selected by the skilled person. Herein below thiol reactive electrophilic group means any group that under aqueous conditions at physiological pH is capable of forming a covalent bond with a thiol (SH) group, in particular the thiol group of a cysteine. Preferably the thiol reactive, electrophilic group is selected from the group that consists of halomethyl ketones, α,β-unsaturated ketones, α,β-unsaturated esters, αβ-unsaturated sulfones, α,β-unsaturated amides, α,β-unsaturated sulfonamides, α,β-unsaturated cyanides, vinylphosphonates, vinylphosphonic acids, aziridines, maleimides, diazomethyl ketones, epoxides and amidines.

In an even more preferred embodiment, the thiol reactive or electrophilic group is a halogeno-amidine group. The term halogeno-amidine herein means a group possessing the structural element —NH—C(=NH)—CH$_2$—X in which X is halogen. Consequently, O(FA) or fluoroamidine means an amino acid with the following side chain: —$CH_2$—$CH_2$—$CH_2$—NH—C(=NH)—$CH_2$—F and O(CA) or chloroamidine means an amino acid with the following side chain: —$CH_2$—$CH_2$—$CH_2$—NH—C(=NH)—$CH_2$—Cl. The halogenoamidine group may be a fluoroamidine, a chloroamidine, an iododamidine or a bromoamidine. Best results were obtained with a fluoroamidine.

In an even more preferred embodiment, the thiol reactive electrophilic group is carried by an amino acid Ω as identified herein. Most preferably, Ω is ornithine. Therefore, in a most preferred compound, ornithine carries an electrophilic group or trap being a halogeno-amidine group, the halogenoamidine group being a fluoroamidine, a chloroamidine, a iodoamidine or a bromoamidine. Even more preferred is a compound wherein said ornithine carries a fluoroamidine or a chloroamidine. Most preferred is a compound wherein said ornithine carries a fluoroamidine.

It is well within the ambit of the skilled person to attach a spacer to a peptide, for example coupling of a spacer to a carboxylic acid, hydroxyl, thiol and amine group that are commonly found in peptides, is routine work. Usually free amine groups are very suitable to attach spacers. Also coupling of spacers to electrophilic groups, preferably spacers to thiol-reactive electrophilic group that react with thiol groups will involve no more than routine experimentation and requires no further specification here.

The spacer connecting the peptide part of a PAD inhibitory molecule according to the invention to the electrophilic group, preferably to the thiol-reactive electrophilic group may represent a connecting group that consists of a linear or branched, saturated or (multiple) unsaturated chain containing 1-12 carbon atoms; in which optionally 4-6 of the atoms together may form a saturated or aromatic ring; and/or in which optionally 1-6 of the carbon atoms may have been replaced by 1-4 N-, O- or S-atoms or combinations thereof. More preferably, the spacer is a group consisting of a branched or linear saturated or (multiple) unsaturated chain containing 3-8 carbon atoms; in which optionally 4-6 of the atoms together may form a saturated or aromatic ring; and/or in which optionally 1-3 of the carbon atoms may have been replaced by 1-3 N-, O- or S-atoms or combinations thereof.

In a preferred embodiment the spacer between the peptide backbone and the electrophilic trap or the electrohilic group or the thiol-reactive electrophile group is a linear saturated aliphatic chain comprising of 3 to 6 carbon atoms.

In order to ensure a sufficient half-life of the molecules according to the invention that are capable of inhibiting PAD activity in vitro and in vivo, the peptide part of the molecule is preferably modified to ensure a reduced bio-degradability and a sufficient bio-availability. Alternatively the peptide may be circularized, to avoid peptidase degradation at the termini for instance. Also non natural occurring amino acids and/or amino acids normally not present in the human body, or peptide-mimetics, may be used in the peptide part of the molecule to prevent degradation and/or enhance chemical or biological stability and bio-availability. The peptide part of the PAD inhibitory molecule may comprise D-amino acids, β-amino acids, α-methyl amino acids and/or α-alkenyl amino acids to prevent, delay or inhibit bio-degradation after administration of the compound to a subject to be treated.

Modification of the C- and/or N-Terminus of the Peptide Part

In a compound according to the invention, the carboxy terminus of the peptide may be modified or extended with a protective group, which will prevent enzymatic degradation and/or increase chemical stability and/or solubility in aqueous solutions. A compound of the invention may comprise a C-terminal protective group that is a linear or branched alkyl, aryl or alkylaryl group, optionally containing N, O, S or halogen substituted moieties, in total comprising 3 to about 25 atoms.

Preferably a C-terminal protective group is chosen from the group consisting of $NH_2$, NH—$NH_2$, $NHR_{1-8}$, NH—$NHR_{1-8}$, $CH_2CN$, $R_{1-8}$, O—$R_{1-8}$, $CHR_{1-8}R_{1-8}$, $CR_{1-8}R_{1-8}R_{1-8}$, $NR_{1-8}R_{1-8}$ and $CH_2$—$NR_{1-8}R_{1-8}$, wherein independently for each $R_{1-8}$ one $R_1$ to $R_8$ as described below is chosen, and wherein;

$R_1$ represents a branched or linear saturated or (optionally multiple) unsaturated chain containing 1-12 carbon atoms;

$R_2$ represents an alkyl group containing 1-12 carbon atoms in which 4-8 of the carbon atoms form a cyclic moiety;

$R_3$ represents $R_1$ or $R_2$ in which up 1-4 carbon atoms have been replaced by N-, O- or S-atoms or combinations thereof;

$R_4$ represents an aryl, bisaryl or fused aryl group containing 6-12 ring carbon atoms;

$R_5$ represents $R_4$ in which 1-4 carbon atoms have been replaced by N-, O- or S-atoms or combinations thereof;

$R_6$ represents an alkylaryl group in which the alkyl part is linear, branched or cyclic and consists of 1-6 carbon atoms and the aryl part consists of 6 carbon atoms;

$R_7$ represents $R_6$ in which 1-3 atoms in the alkyl part and/or 1-4 atoms in the aryl part have been replaced by N-, O- or S-atoms or combinations thereof; and, $R_8$ represents $R_1$ to $R_7$ which are substituted with 1-4 additional substituents, which are selected from the group that consists of ($C_1$-$C_6$)alkyl, ($C_3$-$C_6$)cycloalkyl, ($C_1$-$C_6$)alkenyl, ($C_1$-$C_6$)alkynyl, ($C_1$-$C_6$)alkoxy, ($C_1$-$C_6$)thioalkoxy, nitro, halogen and a heterocyclic group with 4-6 ring atoms of which 1-5 are carbon atoms and 1-3 are N-, O- or S-atoms or combinations thereof.

The peptide part of a compound according to the invention may also be protected at the amino terminus of the peptide. The amino terminus may be modified or extended with a protective group, wherein the N-terminal protective group may be a linear or branched alkyl, aryl or alkylaryl group, optionally containing N, O, S or halogen substituted moieties, in total comprising 3 to about 25 atoms. Preferably the N-protective group is chosen from the group consisting of $R_{1-8}$—C(O), $R_{1-8}$—O—C(O), $R_{1-8}$, $R_{1-8}$—$SO_2$, or two of such protective groups which may be the same or different may be present, wherein independently for each $R_{1-8}$ one of $R_1$ to $R_8$ as described below is chosen, in which:

$R_1$ represents a branched or linear saturated or (optionally multiple) unsaturated chain containing 1-12 carbon atoms;

$R_2$ represents an alkyl group containing 1-12 carbon atoms in which 4-8 of the carbon atoms form a cyclic moiety;

$R_3$ represents $R_1$ or $R_2$ in which up 1-4 carbon atoms have been replaced by N-, O- or S-atoms or combinations thereof;

$R_4$ represents an aryl, bisaryl or fused aryl group containing 6-12 ring carbon atoms; preferably $R_4$—$SO_2$ or 2-naphtylsulfonyl group wherein $R_4$ is an aryl group with 10 carbon atoms (i.e. naftyl group);

$R_5$ represents $R_4$ in which 1-4 carbon atoms have been replaced by N-, O- or S-atoms or combinations thereof;

$R_6$ represents an alkylaryl group in which the alkyl part is linear, branched or cyclic and consists of 1-6 carbon atoms and the aryl part consists of 6 carbon atoms;

R$_7$ represents R$_6$ in which 1-3 atoms in the alkyl part and/or 1-4 atoms in the aryl part have been replaced by N-, O- or S-atoms or combinations thereof; and, R$_8$ represents R$_1$ to R$_7$ which are substituted with 1-4 additional substituents, which are selected from the group that consists of (C$_1$-C$_6$)alkyl, (C$_3$-C$_6$)cycloalkyl, (C$_1$-C$_6$)alkenyl, (C$_1$-C$_6$)alkynyl, (C$_1$-C$_6$)alkoxy, (C$_1$-C$_6$) thioalkoxy, nitro, halogen and a heterocyclic group with 4-6 ring atoms of which 1-5 are carbon atoms and 1-3 are N, O- or S-atoms or combinations thereof.

As a preferred embodiment, a compound of the invention is such that the N-terminus of the peptide sequence is modified by an acetyl group and/or the C-terminus as an amide. These compounds were found to have an increased stability as inhibitor.

As another preferred embodiment, a compound of the invention is such that the N-terminus of the peptide sequence is modified by the addition of a 2-naphtylsulfonyl group. Such compounds have attractive properties since they have an increased stability as inhibitor and have been surprisingly found to have improved inhibitory activity or improved efficacy as an inhibitor of PAD2 and PAD4 (see example 9). Preferred compounds of the invention comprises a peptide part, said peptide part comprising or consisting of the sequences SEQ ID NO: 115 or 119 as identified in table 23 in example 9.

As another preferred embodiment, a compound of the invention is such that the C-terminus of the peptide sequence is modified by the addition of a D-amino acid. Such compounds have attractive properties since they have an increased stability as inhibitor and have been surprisingly found to have inhibitory activity which is not affected by this modification (see example 9). Preferred compounds of the invention comprises a peptide part, said peptide part comprising or consisting of the sequences SEQ ID NO: 120-127 as identified in table 26 in example 9.

As a more preferred embodiment, a compound of the invention is such that the N-terminus of the peptide sequence is modified by the addition of a 2-naphtylsulfonyl group and the C-terminus of the peptide sequence is modified by the addition of a D-amino acid. Preferred compounds of the invention comprises a peptide part, said peptide part comprising or consisting of the sequences SEQ ID NO: 128-135 as identified in table 28 in example 9.

In order to increase the solubility of the peptide part, which may be insufficiently soluble when several apolar amino acids are present, the peptide part may be modified by addition of solubility enhancing polar groups, in particular at the N- and/or C-terminus of the peptide part. The solubilizing group is preferably a spacer moiety located between the N- and/or C-terminus of the peptide part and the N- or C-terminal protective group. In a most preferred embodiment, the solubilizing group represents a polar spacer moiety with the structure NH—(CH$_2$—CH$_2$—O—)$_m$—(CH$_2$)$_n$—C(O) in which m=1-6 and n=0, 1 or 2.

Although PAD activity may be inhibited in the extracellular space, PAD inhibition may also take place intracellularly, for instance to inhibit citrullination of histones and other substrates, for instance to alter gene expression. In order to facilitate or enhance cellular uptake of PAD inhibitory molecules according to the current invention, in another embodiment the inhibitory peptide molecules may be fused to protein transduction domains or to cell penetrating peptides. Several proteins and small peptides have the ability to transduce or travel through biological membranes independent of classical receptor- or endocytosis-mediated pathways. Examples of these proteins include the HIV-1 TAT protein, the herpes simplex virus 1 (HSV-1) DNA-binding protein VP22, and the Drosophila Antennapedia (Antp) homeotic transcription factor. The small protein transduction domains (PTDs) from these proteins can be fused to other macromolecules, peptides or proteins to successfully transport them into a cell, including the polypeptides and modified polypeptides according to this specification. Sequence alignments of the transduction domains show a high basic amino acid content (Lys and Arg) which may facilitate interaction of these regions with negatively charged lipids in the membrane. Secondary structure analyses show no consistent structure between all three domains.

A compound according to the invention is capable of inhibiting a PAD enzyme, in vitro and/or in vivo, intracellularly and/or extracellularly. PAD2 and/or PAD4 are most preferred since these enzymes are enzymes involved in an autoimmunity related citrullination process.

Composition

In another aspect, the invention provides a composition comprising a compound as earlier defined herein and at least one excipient, said composition is preferably a pharmaceutical composition or a medicament for the treatment and/or prevention of an autoimmune disorder, preferably in humans. Said composition or compound may also be used to delay the development of such disorder. Autoimmune disorders are diseases in which the immune system targets an endogenous antigen, with consequent injury to tissues. Aberrant citrullination often plays a role in the recognition of autoantigens by the immune system of a subject. A compound or composition according to the invention may be used for the manufacture of a medicament for the treatment or prevention of a PAD related and/or citrullination related disease or disorder, or a PAD exacerbated disease or disorder. In particular, a PAD inhibitory compound or a composition according to the invention may be used for the manufacture of medicaments for the treatment of an autoimmune disorder, such as, but not limited to RA, MS, psoriasis, systemic lupus erythematosus (SLE), Hashimoto's thyroiditis, Graves' disease, systemic sclerosis (scleroderma), neonatal lupus syndromes, idiopathic inflammatory myopathies, juvenile chronic arthritis, psoriatic arthritis, autoimmune hepatitis, mixed connective tissue disease (MCTD), Sjögren's syndrome and Wegener's granulomatosis.

A compound according to the invention may be formulated with pharmaceutically acceptable excipients. Therefore a composition of the invention comprises a compound of the invention and at least one excipient. Formulation of pharmaceutical compositions suitable for various modes of administration, parenteral or oral, is known in the art and described in various textbooks such as Remmington Pharmaceutical Sciences, Mack publishing co., 1989. A pharmaceutical composition may be suitably adapted by the skilled artisan for a given compound according to the invention, and/or for the autoimmune disorder to be treated, and/or for the mode of administration/location in the body. It may be preferable to combine a PAD inhibitory compound of the invention in a pharmaceutical composition or formulation with other active compounds, such as immuno-suppressant agents and/or an inflammation suppressant agent. Preferred example of immunosuppressant compounds that may be used in combination with PAD inhibitory molecules of the invention are Azathioprine (Imuran), Cyclosporine (A), Mercaptopurine (Purinethol, 6-MP), preferred examples of inflammation suppressant agents are NSAIDs (non steroid anti-inflammatory drugs) or corticosteroids such as prednisolone.

In a preferred embodiment a pharmaceutical composition according to the invention is a composition for the treatment of RA and is a composition for parenteral, preferably topical administration such as ointment or depository formulations which may be applied topically on inflamed joints. Most preferably such compositions comprise excipients that allow transdermal administration of a PAD inhibitory compound, for instance a formulation in liposomes. In another preferred embodiment, a composition according to the invention is a composition for the treatment of RA and is a composition for parenteral, preferably topical administration by injection into the RA affected and/or inflamed joint, preferably directly into the synovial fluid of the joint, or optionally by replacing the synovial fluid in a joint, at concentrations between 1 μg to 0.1, 0.5, 1, 2, 5, 10 mg per injection in a single dose, depending on the affinity and activity of a compound, the size of the joint in the subject and severity of the inflammation. However, given the high specificity of an inhibitory molecule or compound of the invention, little side effects are anticipated and systemic administration of PAD inhibitors via oral ingestion or intravenous or intramuscular injections are other feasible routes of administration.

In particular, a medicament according to the invention may be used in methods of treatment and/or prevention of an autoimmune disease as mentioned before, in a subject, preferably a human and most preferably for the treatment of RA and MS.

In the context of the invention, an organism or an individual or a subject to be treated may be an animal or a human being. Preferably, the organism is a human being. Preferably, an organism treated is suspected to have a high risk of developing an autoimmune disorder such as RA, due for example to potential genetic predisposition, and/or to the age of the subject and/or to the lifestyle of a subject (for example nutritional habit and/or to the absence of physical activity).

The term "prevention" shall be understood to include complete prevention, prophylaxis, as well as lowering the individual's risk of falling ill with said disease or condition. The term shall also be understood to include alleviation of symptoms already developed.

The term "delaying" used herein means administration of the compound to an organism, i.e. a patient being in a pre-stage of the condition to be treated in which patients a pre-form of the corresponding condition is diagnosed by methods known in the art. Preferably, the apparition of the symptoms of the disease, are delayed of at least several months to one year or more. The term "treatment" or "treating" "is understood the management and care of a patient for the purpose of combating the disease, condition, or disorder.

Each compound of the invention as defined herein is suitable to be used to prevent, delay and/or treat an autoimmune disorder as defined herein.

Accordingly in a preferred embodiment, a compound or a composition of the invention are for use as a medicament as defined earlier herein.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

In addition the verb "to consist" may be replaced by "to consist essentially of" meaning that a compound or a composition as defined herein may comprise additional component(s) than the ones specifically identified, said additional component(s) not altering the unique characteristic of the invention. Within the context of the invention, the word "about" when used in the context of a compound (i.e. about 5 amino acids) means that there is 5 to 6 amino acids.

All patent and literature references cited in the present specification are hereby incorporated by reference in their entirety. The following examples are offered for illustrative purposes only, and are not intended to limit the scope of the present invention in any way.

BRIEF DESCRIPTION OF THE DRAWINGS

FIG. 5. This figure illustrates the mass spectrometry data observed for the PAD-mediated conversion of peptide D-S-K-K-F-H-R-G-F-L-Y-S-D (SEQ ID NO: 90) (0708-33, $MH2^{2+}_{calc}=800.39$, $MH3^{3+}_{calc}=533.93$) into its citrulline variant ($\Delta M=0.98$ Da).

A: Mass spectrum of substrate peptide D-S-K-K-F-H-R-G-F-L-Y-S-D (SEQ ID NO: 90) (top) and product peptide D-S-K-K-F-H-Cit-G-F-L-Y-S-D (SEQ ID NO: 144) (bottom) at 100% conversion by PAD.

B: Enlargement of $3^+$-signals.

C: Enlargement of $2^+$-signals.

Figure 6:
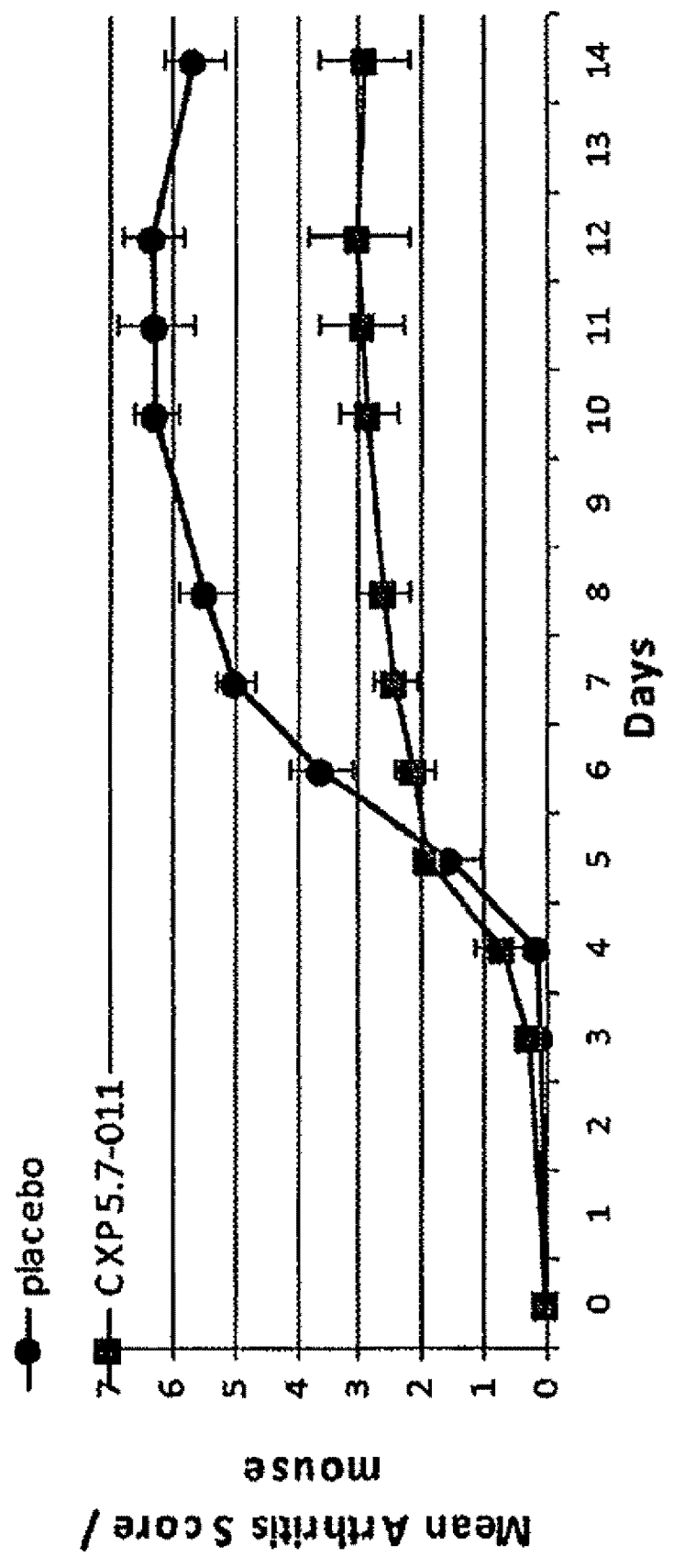

FIG. 6. The collagen antibody induced arthritis (CAIA) model (MQR; 18.101) was used to test the therapeutic effect of the PAD-inhibitor CXP5.7-011 (SEQ ID NO:143). At day 0 mice were injected i.p. with 2.8 mg anti-collagen antibodies. LPS (25 μg/mouse) was administered on day 3 via i.p. injection. The inhibitor (0.5 mg CXP5.7-011 in 200 μl PBS containing 20 mM sodium phosphate), or 200 μl PBS containing 20 mM sodium phosphate as the placebo, was administered daily from day 3 until day 11 (with the exception of day 9). Animals were scored daily until day 14 for degree of inflammation. Mean arthritis score per experimental group (5 mice) is indicated at each time point.

EXAMPLES

Example 1

Inhibitors Based on Natural Substrates

Figure 1:
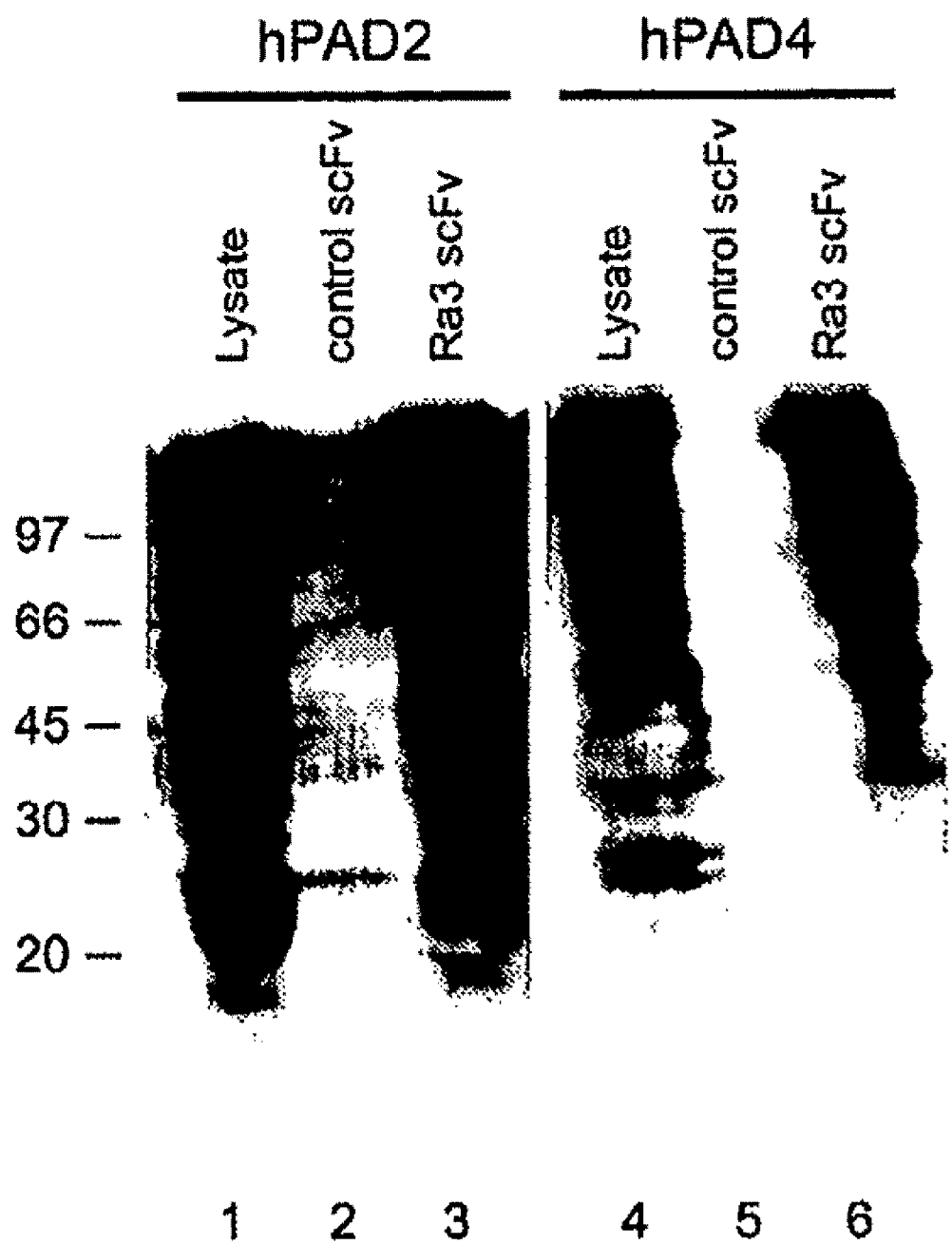
FIG. 1. Lysates of COS-1 cells expressing either the human PAD2 or PAD4 protein were incubated at 37° C. for 30 minutes in the presence of 10 mM CaCl12. The citrullination of proteins in the lysates was visualized by SDS-PAGE/western blotting, followed by modification of citrulline residues and incubation with anti-modified citrulline antibodies (lanes 1 and 4). Citrullinated proteins were isolated from the lysates by immunoaffinity purification using the Ra3 scFv antibody (lanes 3 and 6), and an unrelated scFv (directed to GST) as a negative control (lanes 2 and 5), and analysed in parallel.

Several substrates for PAD have been identified on the protein level. It has been shown that in vivo in particular arginines in proteins can be converted to citrulline (Cit), whereas other arginines seem to be completely resistant to conversion into citrulline. From these observations it is clear that the chemical surroundings of an arginine residue determine its substrate properties. To investigate the identity of the flanking amino acids that are most frequently found in the surroundings of arginines that are converted by PAD enzymes, cDNAs encoding the human PAD2 and PAD4 were cloned in the eukaryotic expression vector pCI-NEO (Promega, Leiden, The Netherlands) in frame with a sequence encoding the VSV-G tag. Cultured COS-1 or HEK293 cells were transfected with the resulting constructs and the expression of PADs in these cells was verified by immunoblotting, using extracts from the cells prepared 48 hours after transfection and monospecific anti-PAD antisera raised in rabbits. The results showed that both PAD2 and PAD4 were efficiently expressed in these cells. The analysis of extracts of these cells with anti-modified citrulline antibodies (AMC), after treatment of the western blots with the reagents that modify peptidylcitrulline {Senshu et al., 1992} revealed that, as expected based upon the low calcium concentrations in the cell, no citrullinated proteins could be detected. To allow citrullination of cellular proteins to occur, the cells were lysed in a buffer containing 20 mM Tris-HCl, pH 7.4, 10 mM β-mercaptoethanol, 100 mM NaCl, 10% glycerol and EDTA-free protease inhibitor, and the lysate was subsequently incubated for 30 minutes at 37° C. after the addition of calcium chloride to a final concentration of 10 mM. As a control, the lysates were incubated in parallel in the presence of 5 mM EDTA. Immunoblot analysis with the AMC antibodies, after treatment of the proteins electro-transferred onto reinforced nitrocellulose membranes with the chemical modification mixture. revealed that this procedure led to calcium- and PAD-dependent citrullination of multiple cellular proteins in the lysate (FIG. 1).

Importantly, differences were observed in the pattern of citrullinated proteins obtained for the different PAD enzymes, indicating that differences exist in the substrate specificity of PAD2 and PAD4. Subsequently, the citrullinated proteins were isolated from the cell lysates by immunoaffinity purification using the RA3 single chain antibody fragment (scFv), which is specific for citrullinated epitopes {Raats et al., 2003}. After digestion of the purified proteins with trypsin, the amino acid sequence of the resulting peptides was determined by tandem mass spectrometry. Based upon the mass spectrometry data the peptides containing citrullinated residues were identified. In total 90 and 57 citrullinated peptides were identified in proteins derived from the COS-1 cells expressing PAD2 and PAD4, respectively, and 107 and 38 citrullinated peptides were obtained from HEK-293 cell material for PAD2 and PAD4, respectively. The frequency of amino acids at each of the positions between 5 residues N-terminal and 5 residues C-terminal from a citrullinated residue was derived from the combined sequences of these sites and is illustrated in Table 1. Based upon these data PAD2- and PAD4-specific 13-mer peptides were synthesized that contained the arginine at the central position (Table 2). The efficiency by which these peptides were citrullinated by the human PAD2 and PAD4 enzymes was investigated by incubating them with the bacterially expressed, $His_6$-tagged and IMAC purified, recombinant enzymes, followed by analysis of the products by both MALDI-TOF and ESI-Q-TOF mass spectrometry. The efficiency of citrullination of these peptides is listed in Table 2.

TABLE 1

A. COS-1 cells expressing hPAD2; data derived from 90 peptide sequences.

<0.5
>1.5
>2.0
n/a

| | -5 | -4 | -3 | -2 | -1 | 0 | +1 | +2 | +3 | +4 | +5 |
|---|---|---|---|---|---|---|---|---|---|---|---|
| G | 1.1 | 1.3 | 1.1 | 1.5 | 1.1 | 0.0 | 2.1 | 1.9 | 2.9 | 1.6 | 1.8 |
| A | 1.4 | 0.6 | 0.6 | 1.4 | 0.8 | 0.0 | 1.2 | 1.4 | 0.8 | 0.8 | 0.8 |
| P | 0.9 | 1.3 | 1.3 | 1.6 | 0.9 | 0.0 | 0.7 | 1.1 | 1.6 | 0.9 | 0.2 |
| V | 1.2 | 0.7 | 0.5 | 1.0 | 0.9 | 0.0 | 1.0 | 0.7 | 0.9 | 0.2 | 1.2 |
| L | 0.4 | 0.8 | 0.7 | 0.8 | 1.4 | 0.0 | 0.6 | 0.8 | 0.0 | 0.8 | 0.4 |
| I | 1.4 | 1.5 | 0.6 | 1.0 | 0.8 | 0.0 | 0.6 | 0.4 | 0.8 | 0.2 | 0.6 |
| M | 1.0 | 0.5 | 1.4 | 0.0 | 1.9 | 0.0 | 1.4 | 1.4 | 0.0 | 1.4 | 1.4 |
| F | 0.5 | 0.5 | 1.9 | 0.5 | 0.5 | 0.0 | 0.3 | 0.8 | 1.1 | 0.5 | 1.1 |
| Y | 0.7 | 0.7 | 0.3 | 1.7 | 0.3 | 0.0 | 0.3 | 0.7 | 2.4 | 1.4 | 0.3 |
| W | 0.0 | 0.8 | 0.8 | 0.8 | 2.5 | 0.0 | 0.8 | 0.0 | 0.0 | 0.0 | 0.0 |
| S | 1.7 | 1.7 | 1.2 | 0.6 | 1.5 | 0.0 | 1.5 | 1.5 | 0.8 | 0.9 | 0.8 |
| T | 0.9 | 0.6 | 0.8 | 1.1 | 0.4 | 0.0 | 0.8 | 0.8 | 1.1 | 0.6 | 0.8 |
| C | 0.0 | 0.0 | 0.0 | 0.0 | 0.0 | 0.0 | 0.0 | 0.0 | 0.0 | 0.0 | 0.0 |
| N | 1.0 | 1.2 | 0.2 | 1.2 | 0.2 | 0.0 | 0.7 | 0.2 | 0.2 | 1.0 | 0.2 |
| Q | 0.6 | 1.1 | 1.1 | 0.8 | 0.8 | 0.0 | 1.4 | 0.3 | 1.4 | 0.3 | 0.3 |
| K | 0.6 | 0.4 | 1.7 | 0.4 | 1.0 | 0.0 | 1.5 | 1.5 | 1.7 | 2.7 | 2.7 |
| H | 0.5 | 0.5 | 0.0 | 0.0 | 0.5 | 0.0 | 1.0 | 1.0 | 0.0 | 1.5 | 1.5 |
| R | 1.1 | 1.9 | 1.7 | 0.9 | 1.3 | 19.2 | 1.3 | 1.3 | 1.7 | 1.1 | 2.4 |
| D | 2.4 | 1.3 | 1.3 | 1.3 | 2.2 | 0.0 | 1.1 | 1.7 | 0.4 | 1.1 | 1.1 |
| E | 0.9 | 1.1 | 1.6 | 1.6 | 0.9 | 0.0 | 0.5 | 0.5 | 0.7 | 2.1 | 1.4 |

B. COS-1 cells expressing hPAD4; data derived from 57 peptide sequences.

| | -5 | -4 | -3 | -2 | -1 | 0 | +1 | +2 | +3 | +4 | +5 |
|---|---|---|---|---|---|---|---|---|---|---|---|
| G | 2.0 | 1.8 | 2.0 | 1.8 | 1.0 | 0.0 | 1.8 | 2.9 | 2.2 | 1.6 | 2.4 |
| A | 0.9 | 0.9 | 0.9 | 0.5 | 0.7 | 0.0 | 1.0 | 0.7 | 1.3 | 0.0 | 0.8 |
| P | 1.7 | 0.7 | 0.7 | 0.7 | 0.7 | 0.0 | 0.0 | 1.8 | 1.1 | 1.9 | 0.7 |
| V | 0.5 | 0.3 | 0.3 | 1.1 | 0.5 | 0.0 | 0.3 | 0.8 | 1.1 | 0.3 | 0.0 |
| L | 0.4 | 0.9 | 0.2 | 0.7 | 1.1 | 0.0 | 0.4 | 0.2 | 0.2 | 0.4 | 0.2 |
| I | 0.3 | 0.3 | 0.3 | 0.3 | 0.3 | 0.0 | 0.0 | 0.3 | 0.3 | 0.3 | 0.0 |
| M | 0.7 | 2.2 | 0.0 | 0.7 | 0.7 | 0.0 | 0.8 | 0.8 | 0.8 | 0.8 | 0.8 |
| F | 0.8 | 1.3 | 2.1 | 0.8 | 0.8 | 0.0 | 0.9 | 0.9 | 0.0 | 1.3 | 0.4 |
| Y | 1.1 | 4.8 | 0.5 | 2.7 | 0.5 | 0.0 | 0.0 | 1.7 | 4.6 | 4.0 | 1.1 |
| W | 1.3 | 1.3 | 1.3 | 1.3 | 2.6 | 0.0 | 0.0 | 0.0 | 0.0 | 1.4 | 0.0 |
| S | 1.6 | 0.9 | 2.6 | 3.3 | 2.8 | 0.0 | 1.9 | 1.2 | 0.8 | 1.5 | 2.5 |
| T | 0.3 | 0.3 | 0.6 | 0.3 | 0.0 | 0.0 | 0.0 | 0.3 | 0.3 | 0.0 | 0.9 |
| C | 0.0 | 0.0 | 0.0 | 0.0 | 0.0 | 0.0 | 0.0 | 0.0 | 0.0 | 0.0 | 0.0 |
| N | 0.8 | 0.4 | 0.0 | 1.5 | 0.4 | 0.0 | 2.3 | 0.4 | 0.8 | 0.8 | 0.0 |
| Q | 0.4 | 0.4 | 0.9 | 0.9 | 0.0 | 0.0 | 0.4 | 0.9 | 0.0 | 1.4 | 0.0 |
| K | 0.6 | 1.2 | 2.1 | 0.3 | 0.0 | 0.0 | 0.0 | 0.3 | 0.3 | 1.0 | 0.3 |
| H | 0.0 | 0.8 | 0.0 | 0.0 | 0.0 | 0.0 | 0.0 | 0.0 | 0.0 | 0.0 | 0.8 |
| R | 2.7 | 2.3 | 2.3 | 1.3 | 2.3 | 19.2 | 1.7 | 1.4 | 3.6 | 1.4 | 1.8 |
| D | 1.3 | 0.0 | 1.0 | 0.7 | 2.7 | 0.0 | 4.5 | 2.1 | 1.4 | 1.8 | 1.4 |
| E | 1.4 | 0.8 | 0.6 | 0.3 | 1.7 | 0.0 | 2.0 | 1.5 | 0.6 | 1.2 | 3.3 |

TABLE 1-continued

C. HEK293 cells expressing hPAD2;
data derived from 106 peptide sequences.

<0.5
>1.5
>2.0
n/a

|   | -5 | -4 | -3 | -2 | -1 | 0 | +1 | +2 | +3 | +4 | +5 |
|---|---|---|---|---|---|---|---|---|---|---|---|
| G | 1.7 | 1.0 | 0.1 | 1.1 | 1.4 | 0.0 | 1.1 | 1.5 | 1.1 | 1.3 | 1.6 |
| A | 2.0 | 1.4 | 1.0 | 1.9 | 1.2 | 0.0 | 1.3 | 2.0 | 1.5 | 0.5 | 1.3 |
| P | 1.0 | 0.8 | 1.0 | 2.1 | 0.9 | 0.0 | 1.3 | 1.2 | 1.0 | 1.4 | 1.6 |
| V | 1.0 | 1.0 | 0.7 | 2.2 | 1.2 | 0.0 | 0.9 | 1.2 | 0.6 | 0.6 | 1.2 |
| L | 0.8 | 0.5 | 0.5 | 0.6 | 0.7 | 0.0 | 0.8 | 0.5 | 0.4 | 0.6 | 0.4 |
| I | 1.0 | 1.2 | 0.8 | 0.3 | 0.7 | 0.0 | 1.5 | 1.2 | 0.2 | 0.5 | 0.5 |
| M | 0.0 | 0.0 | 1.2 | 0.0 | 0.4 | 0.0 | 0.8 | 2.1 | 0.4 | 1.3 | 0.4 |
| F | 1.2 | 1.2 | 1.6 | 0.9 | 0.7 | 0.0 | 0.7 | 0.2 | 0.5 | 0.0 | 1.7 |
| Y | 0.9 | 1.2 | 1.8 | 1.2 | 1.5 | 0.0 | 1.2 | 0.9 | 2.1 | 1.5 | 0.6 |
| W | 0.7 | 2.2 | 0.0 | 0.7 | 0.0 | 0.0 | 0.0 | 0.0 | 0.0 | 1.5 | 0.0 |
| S | 0.1 | 1.4 | 1.2 | 0.6 | 0.5 | 0.0 | 0.8 | 0.7 | 1.3 | 0.9 | 0.7 |
| T | 0.5 | 0.5 | 0.5 | 0.2 | 1.0 | 0.0 | 0.8 | 1.2 | 1.3 | 1.5 | 0.5 |
| C | 0.5 | 1.1 | 0.0 | 1.1 | 1.1 | 0.0 | 1.1 | 1.1 | 0.0 | 1.1 | 1.1 |
| N | 0.6 | 0.6 | 0.6 | 0.4 | 0.8 | 0.0 | 1.0 | 0.6 | 0.8 | 0.6 | 0.9 |
| Q | 1.2 | 1.2 | 2.4 | 1.0 | 2.1 | 0.0 | 0.2 | 0.7 | 1.0 | 2.2 | 0.8 |
| K | 2.0 | 1.0 | 1.8 | 1.0 | 1.3 | 0.0 | 1.8 | 1.2 | 2.5 | 1.3 | 2.2 |
| H | 0.9 | 0.4 | 0.9 | 0.0 | 0.4 | 0.0 | 0.4 | 0.0 | 0.4 | 0.0 | 0.0 |
| R | 1.1 | 1.5 | 1.1 | 0.9 | 1.3 | 19.2 | 1.3 | 0.9 | 1.9 | 1.9 | 1.9 |
| D | 0.8 | 1.5 | 1.7 | 1.3 | 1.5 | 0.0 | 0.9 | 0.9 | 0.8 | 0.2 | 0.8 |
| E | 0.8 | 0.6 | 0.9 | 1.1 | 0.8 | 0.0 | 0.8 | 0.9 | 0.6 | 1.6 | 0.5 |

D. HEK293 cells expressing hPAD4;
data derived from 38 peptide sequences.

|   | -5 | -4 | -3 | -2 | -1 | 0 | +1 | +2 | +3 | +4 | +5 |
|---|---|---|---|---|---|---|---|---|---|---|---|
| G | 5.7 | 3.4 | 3.8 | 2.7 | 1.9 | 0.0 | 3.1 | 3.5 | 5.2 | 3.4 | 1.9 |
| A | 1.8 | 1.1 | 0.4 | 0.7 | 1.1 | 0.0 | 0.4 | 0.8 | 0.4 | 0.5 | 0.5 |
| P | 1.1 | 0.5 | 0.5 | 1.1 | 0.0 | 0.0 | 0.5 | 0.0 | 0.6 | 1.3 | 0.7 |
| V | 0.0 | 0.4 | 1.2 | 0.4 | 0.8 | 0.0 | 0.8 | 0.0 | 0.0 | 1.0 | 0.5 |
| L | 0.0 | 1.1 | 0.0 | 0.6 | 0.3 | 0.0 | 0.3 | 0.3 | 0.7 | 0.4 | 0.4 |
| I | 0.5 | 0.0 | 0.5 | 0.9 | 0.0 | 0.0 | 0.0 | 0.0 | 0.0 | 0.0 | 1.2 |
| M | 0.0 | 0.0 | 0.0 | 3.4 | 0.0 | 0.0 | 2.3 | 1.3 | 0.0 | 0.0 | 2.9 |
| F | 0.0 | 3.2 | 1.9 | 0.6 | 0.6 | 0.0 | 2.0 | 1.5 | 0.8 | 0.0 | 0.8 |
| Y | 1.6 | 2.4 | 4.9 | 0.0 | 1.6 | 0.0 | 0.8 | 2.8 | 4.0 | 0.0 | 2.1 |
| W | 2.0 | 5.9 | 0.0 | 2.0 | 0.0 | 0.0 | 0.0 | 0.0 | 0.0 | 2.5 | 0.0 |
| S | 1.4 | 1.4 | 1.8 | 2.9 | 3.6 | 0.0 | 1.8 | 4.5 | 2.2 | 2.7 | 2.7 |
| T | 0.0 | 0.4 | 0.9 | 0.4 | 0.4 | 0.0 | 0.0 | 1.0 | 1.1 | 0.6 | 0.0 |
| C | 0.0 | 0.0 | 0.0 | 0.0 | 0.0 | 0.0 | 0.0 | 0.0 | 0.0 | 0.0 | 0.0 |
| N | 0.6 | 1.2 | 0.0 | 0.6 | 0.0 | 0.0 | 1.2 | 0.0 | 0.0 | 0.0 | 0.7 |
| Q | 2.0 | 0.0 | 1.3 | 0.0 | 0.0 | 0.0 | 0.7 | 0.0 | 0.8 | 0.8 | 1.7 |
| K | 0.0 | 0.5 | 0.9 | 0.5 | 0.0 | 0.0 | 0.0 | 0.0 | 0.0 | 0.0 | 0.0 |
| H | 0.0 | 0.0 | 1.2 | 0.0 | 1.2 | 0.0 | 0.0 | 0.0 | 0.0 | 0.0 | 0.0 |
| R | 1.0 | 0.0 | 0.5 | 1.0 | 2.0 | 19.2 | 2.1 | 0.6 | 1.2 | 1.9 | 3.2 |
| D | 0.5 | 0.0 | 0.0 | 1.5 | 3.1 | 0.0 | 2.6 | 0.6 | 0.6 | 1.3 | 0.0 |
| E | 0.4 | 0.4 | 0.0 | 0.4 | 0.8 | 0.0 | 0.4 | 0.5 | 0.0 | 1.6 | 0.5 |

Proteins immunoaffinity purified from citrullinated cell lysates were subjected to mass spectrometry to identify the citrullination sites. The sequences of the citrullinated peptides were aligned and the frequency of amino acids found in the regions flanking the citrullines (from 5 residues N-terminal to 5 residues C-terminal of the citrulline) were determined and normalized for the natural occurrence of amino acids in human proteins. Therefore, values >1 indicate an overrepresentation of the respective amino acids, whereas values <1 indicate that these amino acids are found less frequently at the citrullination sites.

TABLE 2

Citrullination of synthetic peptides by the recombinant human PAD2 and PAD4 proteins as determined by MALDI-TOF and ESI-Q-TOF mass spectrometry.

| SEQ ID NO: | Sequence | Designed for | PAD2 conversion | | | PAD4 conversion | | |
|---|---|---|---|---|---|---|---|---|
| | | | Arg | 1 Cit | 2 Cit | Arg | 1 Cit | 2 Cit |
| 1 | DDYSSSRDGYGGS | PAD4 | 88% | 12% | — | 97% | 3% | — |
| 2 | GGYSGDRSGGGYG | PAD4 | 33% | 67% | — | 61% | 39% | — |
| 3 | DGYGGSRDSYSSS | PAD4 | 54% | 46% | — | 97% | 3% | — |
| 4 | DSYRSWRDGYYSD | PAD4 | 16% | 30% | 55% | 1% | 99% | 0% |
| 5 | IEIMTDRGSGKKR | PAD2 | 6% | 34% | 60% | 37% | 60% | 3% |
| 6 | IGSRGDRSGFGKF | PAD2 | 1% | 96% | 4% | 2% | 69% | 29% |
| 7 | IEIITDRQSGKKR | PAD2 | 5% | 70% | 25% | 2% | 88% | 10% |
| 8 | DSEGTWRKGPEAD | PAD2 | 15% | 85% | — | 85% | 15% | — |
| 9 | DSSEELRGGGKSD | PAD2 | 43% | 57% | — | 93% | 7% | — |
| 10 | DSRFYWRGGGKSD | PAD2 | 14% | 14% | 73% | 6% | 69% | 25% |
| 11 | DSQFAFRGASASD | PAD4 (L1) | 68% | 32% | — | 98% | 2% | — |

Table 2 comprises peptides represented by the following sequences SEQ ID NO:1-10. SEQ ID NO: 11 represents the control L1.

The following amino acid sequences were chosen for the synthesis of inhibitors:

```
I-E-I-M-T-D-R-G-S-G-K-K-R      (SEQ ID NO 5)
and

I-G-S-R-G-D-R-S-G-F-G-K-F      (SEQ ID NO 6)
for PAD2

D-D-Y-S-S-S-R-D-G-Y-G-G-S      (SEQ ID NO 1)
and

G-G-Y-S-G-D-R-S-G-G-G-Y-G      (SEQ ID NO 2)
for PAD4
```

Initially 8 pentapeptides inhibitors derived from these sequences were evaluated:

```
T-D-O(FA)-G-S      (SEQ ID NO: 12)

G-D-O(FA)-S-G      (SEQ ID NO: 13)

S-S-O(FA)-D-G      (SEQ ID NO: 14)

G-S-O(FA)-D-G      (SEQ ID NO: 15)

T-D-O(CA)-G-S      (SEQ ID NO: 16)

G-D-O(CA)-S-G      (SEQ ID NO: 17)

S-S-O(CA)-D-G      (SEQ ID NO: 18)

G-S-O(CA)-D-G      (SEQ ID NO: 19)
```

These 8 pentapeptides inhibitors are represented by SEQ ID NO: 12-19. (O(FA) stands for ornithine fluoroamidine, O(CA) stands for ornithine chloroamidine). The $IC_{50}$'s for human PAD2 and 4 as well as for mouse PAD2 and 4 were determined in an assay developed by Zendman and others {Zendman et al. 2007}. Of this series the inhibitor T-D-O(FA)-G-S(CXP5-101) (SEQ ID NO: 12) was the best PAD2 and PAD4 inhibitor. Subsequently, several modifications were brought to this lead compound. A second round of screening showed that G-D-O(CA)-G-S (CXP5.2-078) (SEQ ID NO:20) and Y-D-O(CA)-G-S(CXP5.2-081)(SEQ ID NO:21) were more potent than T-D-O(FA)-G-S (SEQ ID NO 12). Also Ac-G-D-O(CA)-G-S-amide (CXP5.7-012) (SEQ ID NO: 142) and Ac-Y-D-O(CA)-G-S-amide (CXP5.7-011) (SEQ ID NO:143) were synthesized because they were expected to possess higher in vivo stability (see Example 10).

In order to compare the best inhibitors to Cl-amidine, a PAD 4 inactivator recently published {Luo et al., 2006}, a colorimetric assay was developed (see example 6).

Example 2

Inhibitors Based on Non-Natural Substrates

From previous studies it was known that D-S-Q-F-A-F-R-G-A-S-A-S-D (designated here as L1: SEQ ID NO: 11) is a substrate for PAD2 and PAD 4. To obtain better substrates, and subsequently powerful inhibitors, we intended to identify structural elements that improve substrate properties. A set of 152 individual analog peptides was generated, each differing from L1 by one amino acid at one of the positions −4 to −1 or 1 to 4.

In Table 3 the conversion of each analog (R to Cit conversion) is depicted. Values of the analogs relate to the conversion of the analog compared to the conversion of L1 under standard conditions (100 means a conversion equal to L1, 50 means conversion of 50% of that of L1, 175 means conversion of 175% of that of L1). Numbers above 100 thus relate to amino acid substitutions that improve substrate properties.

TABLE 3

| | conversion of L1 analogs by PAD4 | | | | | | | | | | | |
|---|---|---|---|---|---|---|---|---|---|---|---|---|
| | −6 | −5 | −4 | −3 | −2 | −1 | | 1 | 2 | 3 | 4 | 5 | 6 |
| | D | S | Q | F | A | F | R | G | A | S | A | S | D |
| A | | | 80 | 80 | 100 | 75 | | 15 | 100 | 100 | 100 | | |
| C | | | 80 | 100 | 150 | 100 | | 50 | 115 | 150 | 125 | | |
| D | | | 40 | 80 | 40 | 190 | | 150 | 100 | 110 | 110 | | |
| E | | | 60 | 60 | 70 | 90 | | 115 | 100 | 140 | 125 | | |
| F | | | 130 | 100 | 160 | 100 | | 15 | 130 | 150 | 150 | | |
| G | | | 80 | 100 | 80 | 75 | | 100 | 100 | 100 | 100 | | |
| H | | | 165 | 180 | 165 | 210 | | 50 | 130 | 140 | 10 | | |
| I | | | 80 | 80 | 90 | 0 | | 15 | 0 | 150 | 100 | | |
| K | | | 190 | 230 | 165 | 100 | | 10 | 60 | 130 | 110 | | |
| L | | | 120 | 100 | 150 | 75 | | 0 | 100 | 175 | 100 | | |
| M | | | 100 | 80 | 140 | 75 | | 15 | 100 | 150 | 110 | | |
| N | | | 80 | 60 | 120 | 100 | | 60 | 65 | 100 | 100 | | |
| P | | | 120 | 40 | 60 | 50 | | 0 | 35 | 125 | 100 | | |
| Q | | | 100 | 80 | 120 | 25 | | 35 | 65 | 110 | 110 | | |
| R | | | 265 | 180 | 160 | 100 | | 25 | 110 | 10 | 175 | | |
| S | | | 110 | 40 | 100 | 150 | | 50 | 90 | 100 | 100 | | |
| T | | | 90 | 40 | 100 | 90 | | 25 | 85 | 100 | 110 | | |
| V | | | 90 | 40 | 80 | 50 | | 0 | 75 | 150 | 90 | | |
| W | | | 160 | 120 | 150 | 75 | | 50 | 140 | 125 | 150 | | |
| Y | | | 100 | 40 | 120 | 100 | | 25 | 130 | 110 | 150 | | |

Based on the above results we designed 25 peptides containing multiple amino acids that improve substrate properties (see Table 4). The indicated peptides were synthesized and tested in order to identify the best substrate from this group.

TABLE 4

| Peptide code | SEQ ID NO: | Sequence | Conversion (%) |
|---|---|---|---|
| 0608-21 | 22 | D-S-K-H-H-S-R-D-H-L-E-S-D | n.t. |
| 0608-22 | 23 | D-S-K-H-K-D-R-E-Y-V-F-S-D | 90% |
| 0608-23 | 24 | D-S-K-H-F-H-R-D-F-I-Y-S-D | n.t. |
| 0608-24 | 25 | D-S-K-H-L-S-R-E-W-M-W-S-D | 90% |
| 0608-25 | 26 | D-S-K-H-W-D-R-D-H-F-E-S-D | n.t. |
| 0608-26 | 27 | D-S-K-H-H-R-E-Y-L-F-S-D | n.t. |
| 0608-27 | 28 | D-S-K-H-K-S-R-D-F-V-Y-S-D | n.t. |
| 0608-28 | 29 | D-S-K-H-F-D-R-E-W-I-W-S-D | n.t. |
| 0608-29 | 30 | D-S-K-K-L-H-R-D-H-M-E-S-D | n.t. |
| 0608-30 | 31 | D-S-K-K-W-S-R-E-Y-F-S-D | 90% |
| 0608-31 | 32 | D-S-K-K-H-D-R-D-F-L-Y-S-D | 100% (=L2) |
| 0608-32 | 33 | D-S-K-K-H-R-E-W-V-W-S-D | n.t. |
| 0608-33 | 34 | D-S-K-K-F-S-R-D-H-I-E-S-D | n.t. |
| 0608-34 | 35 | D-S-H-K-L-D-R-E-Y-M-F-S-D | 90% |
| 0608-35 | 36 | D-S-H-K-W-H-R-D-F-F-Y-S-D | n.t. |
| 0608-36 | 37 | D-S-H-K-H-S-R-E-W-L-W-S-D | 90% |
| 0608-37 | 38 | D-S-H-H-K-D-R-D-H-V-E-S-D | n.t. |
| 0608-38 | 39 | D-S-H-H-F-H-R-E-Y-I-F-S-D | 90% |
| 0608-39 | 40 | D-S-H-H-L-S-R-D-F-M-Y-S-D | 95% |
| 0608-40 | 41 | D-S-H-H-W-D-R-E-W-F-W-S-D | 100% |
| 0608-41 | 42 | D-S-H-K-H-H-R-D-H-L-E-S-D | n.t. |
| 0608-42 | 43 | D-S-H-K-K-S-R-E-Y-V-F-S-D | n.t. |
| 0608-43 | 44 | D-S-H-K-F-D-R-D-F-I-Y-S-D | 100% |
| 0608-44 | 45 | D-S-H-K-L-H-R-E-W-M-W-S-D | 95% |
| 0608-45 | 46 | D-S-H-K-W-S-R-D-H-F-E-S-D | n.t. |
| 0308-29 | 11 | D-S-Q-F-A-F-R-G-A-S-A-S-D | 30% (=L1) |

Peptides of table 4 are represented by the following sequences SEQ ID NO: 22-31 and 33-46. Control peptide are represented by the following sequences SEQ ID NO: 11 as control L1 and SEQ ID NO: 32 as control L2. Unfortunately, a substantial number of designed peptides were too polar to be analyzed on our LC-MS system (indicated in Table 4 as n.t., not trapped on the column). We therefore also generated and tested these peptides containing two additional N-terminal F-residues to increase hydrophobicity. In this form peptides were trapped on the column and could be analyzed (see Table 5).

TABLE 5

| Peptide code | SEQ ID NO: | Sequence | Conversion (%) |
|---|---|---|---|
| 0612-23 | 47 | F-F-D-S-K-H-H-S-R-D-H-L-E-S-D | 100 |
| 0612-24 | 48 | F-F-D-S-K-H-K-D-R-E-Y-V-F-S-D | 100 |
| 0612-25 | 49 | F-F-D-S-K-H-F-H-R-D-F-I-Y-S-D | 100 |
| 0612-26 | 50 | F-F-D-S-K-H-L-S-R-E-W-M-W-S-D | 100 |
| 0612-27 | 51 | F-F-D-S-K-H-W-D-R-D-H-F-E-S-D | 100 |
| 0612-28 | 52 | F-F-D-S-K-H-H-H-R-E-Y-L-F-S-D | 100 |
| 0612-29 | 53 | F-F-D-S-K-H-K-S-R-D-F-V-Y-S-D | 100 |
| 0612-30 | 54 | F-F-D-S-K-H-F-D-R-E-W-I-W-S-D | 100 |
| 0612-31 | 55 | F-F-D-S-K-K-L-H-R-D-H-M-E-S-D | 88 |
| 0612-32 | 56 | F-F-D-S-K-K-W-S-R-E-Y-F-S-D | 100 |
| 0612-33 | 57 | F-F-D-S-K-K-H-D-R-D-F-L-Y-S-D | 100 |
| 0612-34 | 58 | F-F-D-S-K-K-K-H-R-E-W-V-W-S-D | 100 |
| 0612-35 | 59 | F-F-D-S-K-K-F-S-R-D-H-I-E-S-D | 97 |
| 0612-36 | 60 | F-F-D-S-H-K-L-D-R-E-Y-M-F-S-D | 100 |
| 0612-37 | 61 | F-F-D-S-H-K-W-H-R-D-F-F-Y-S-D | 100 |
| 0612-38 | 62 | F-F-D-S-H-K-H-S-R-E-W-L-W-S-D | 100 |
| 0612-39 | 63 | F-F-D-S-H-H-K-D-R-D-H-V-E-S-D | 100 |
| 0612-40 | 64 | F-F-D-S-H-H-F-H-R-E-Y-I-F-S-D | not tested |
| 0612-41 | 65 | F-F-D-S-H-H-L-S-R-D-F-M-Y-S-D | 98 |
| 0612-42 | 66 | F-F-D-S-H-H-W-D-R-E-W-F-W-S-D | 100 |
| 0612-43 | 67 | F-F-D-S-H-K-H-H-R-D-H-L-E-S-D | 100 |
| 0612-44 | 68 | F-F-D-S-H-K-K-S-R-E-Y-V-F-S-D | 100 |
| 0612-45 | 69 | F-F-D-S-H-K-F-D-R-D-F-I-Y-S-D | 100 |
| 0612-46 | 70 | F-F-D-S-H-K-L-H-R-E-W-M-W-S-D | 100 |
| 0612-47 | 71 | F-F-D-S-H-K-W-S-R-D-H-F-E-S-D | 100 |

Peptides of table 5 are represented by the following sequences SEQ ID NO:47-71.

From these results it is obvious that this set of peptides contains PAD4 substrates with improved substrate properties compared to L1 (0308-29). In addition, incorporation of the two F-residues seemed to improve substrate properties in particular cases.

Peptide 0608-31 (designated as L2) was chosen as lead compound in order to obtain even better substrates for PAD4.

In a very similar fashion to the method described above, L2 was taken as a lead peptide. Again 152 single amino acid substituted peptides were generated and tested. Results are depicted in Table 6 (for explanation see Table 3).

TABLE 6 conversion of L2 analogs by PAD4

| | -6 D | -5 S | -4 K | -3 K | -2 H | -1 D | 1 R | 2 D | 3 F | 4 L | 5 Y | 6 S | 7 D |
|---|---|---|---|---|---|---|---|---|---|---|---|---|---|
| A | | | 45 | 65 | 75 | 60 | | 95 | 80 | 65 | 125 | | |
| C | | | 120 | 65 | 100 | 120 | | 85 | 90 | 105 | 165 | | |
| D | | | 60 | 50 | 80 | 100 | | 100 | 75 | 95 | 145 | | |
| E | | | 70 | 90 | 80 | 70 | | 80 | 40 | 95 | 140 | | |
| F | | | 85 | 100 | 215 | 125 | | 0 | 100 | 115 | 175 | | |
| G | | | 55 | 55 | 85 | 85 | | 110 | 55 | 95 | 135 | | |
| H | | | 125 | 110 | 100 | 160 | | 60 | 210 | 100 | 145 | | |
| I | | | 85 | 80 | 65 | 5 | | 5 | 100 | 110 | 150 | | |
| K | | | 100 | 100 | 110 | 130 | | 45 | 175 | 70 | 110 | | |
| L | | | 90 | 70 | 100 | 40 | | 25 | 80 | 100 | 110 | | |
| M | | | 80 | 75 | 150 | 100 | | 30 | 85 | 110 | 130 | | |
| N | | | 110 | 75 | 95 | 100 | | 70 | 65 | 90 | 110 | | |
| P | | | 70 | 75 | 25 | 10 | | 25 | 20 | 85 | 140 | | |
| Q | | | 70 | 85 | 90 | 40 | | 45 | 75 | 75 | 125 | | |
| R | | | 105 | 145 | 120 | 100 | | 45 | 105 | 95 | 135 | | |
| S | | | 75 | 80 | 95 | 15 | | 55 | 45 | 100 | 105 | | |
| T | | | 50 | 75 | 85 | 40 | | 30 | 80 | 95 | 95 | | |
| V | | | 75 | 45 | 85 | 50 | | 5 | 60 | 90 | 95 | | |
| W | | | 100 | 135 | 150 | 95 | | 10 | 125 | 100 | 165 | | |
| Y | | | 60 | 95 | 165 | 90 | | 30 | 90 | 100 | 100 | | |

Based on the above results we designed 20 peptides containing multiple amino acids that improve substrate properties (see Table 7). The indicated peptides were synthesized and tested in order to identify the best substrate from this group. Here we used a test system with less enzyme (3 times less) compared to the experiments described above.

TABLE 7

| Peptide code | SEQ ID NO: | Sequence | Conversion |
|---|---|---|---|
| 0708-15 | 72 | D-S-K-K-F-D-R-D-H-L-Y-S-D | 51 |
| 0708-16 | 73 | D-S-K-W-F-D-R-D-H-L-Y-S-D | 70 |
| 0708-17 | 74 | D-S-N-K-H-H-R-D-H-L-Y-S-D | 38 |
| 0708-18 | 75 | D-S-K-W-H-H-R-D-H-L-Y-S-D | 60 |
| 0708-19 | 76 | D-S-N-W-H-H-R-D-H-L-Y-S-D | 45 |
| 0708-20 | 77 | D-S-K-K-H-D-R-D-H-L-W-S-D | 62 |
| 0708-21 | 78 | D-S-K-K-H-D-R-D-H-L-F-S-D | 53 |
| 0708-22 | 79 | D-S-K-K-H-F-R-D-K-L-Y-S-D | 43 |
| 0708-23 | 80 | D-S-W-W-H-K-R-D-K-L-Y-S-D | 18 |
| 0708-24 | 81 | D-S-K-K-H-D-R-D-K-L-F-S-D | 35 |
| 0708-25 | 82 | D-S-K-K-F-H-R-D-F-L-Y-S-D | 56 |
| 0708-26 | 83 | D-S-K-K-F-K-R-D-F-L-F-S-D | 23 |
| 0708-27 | 84 | D-S-K-K-F-D-R-D-F-L-F-S-D | 51 |
| 0708-28 | 85 | D-S-H-K-F-D-R-D-F-L-Y-S-D | 53 |
| 0708-29 | 86 | D-S-K-K-Y-D-R-D-F-L-W-S-D | 61 |
| 0708-30 | 87 | D-S-K-K-F-D-R-G-H-L-Y-S-D | 63 |
| 0708-31 | 88 | D-S-K-W-H-H-R-G-H-L-Y-S-D | 52 |
| 0708-32 | 89 | D-S-K-K-H-F-R-G-K-L-Y-S-D | 24 |
| 0708-33 | 90 | D-S-K-K-F-H-R-G-F-L-Y-S-D | 60 |
| 0708-34 | 91 | D-S-K-K-Y-D-R-G-F-L-W-S-D | 64 |
| 0608-31 | 32 | D-S-K-K-H-D-R-D-F-L-Y-S-D | 45 (=L2) |

Peptides of table 7 are represented by the following sequences SEQ ID NO: 72-91 and SEQ ID NO: 32 as control (L2).

These results indicate that the second optimization round didn't provide peptide substrates with significantly improved substrate properties.

In a similar fashion as for PAD4 we identified improved peptide substrates for PAD2. Again L1 was used as a lead compound. The set of 152 peptides from Table 3 was used and testing was performed as described before.

TABLE 8 conversion of L1 analogs by PAD2

| | -6 D | -5 S | -4 Q | -3 F | -2 A | -1 F | 1 R | 2 G | 3 A | 4 S | 5 A | 6 S | 7 D |
|---|---|---|---|---|---|---|---|---|---|---|---|---|---|
| A | | | 145 | 50 | 100 | 25 | | 140 | 100 | 145 | 100 | | |
| C | | | 170 | 225 | 185 | 50 | | 200 | 185 | 225 | 155 | | |
| D | | | 125 | 30 | 95 | 15 | | 140 | 80 | 50 | 115 | | |
| E | | | 130 | 65 | 115 | 15 | | 25 | 70 | 30 | 100 | | |
| F | | | 190 | 100 | 185 | 100 | | 175 | 200 | 260 | 200 | | |
| G | | | 130 | 130 | 105 | 5 | | 100 | 200 | 95 | 160 | | |

TABLE 8-continued conversion of L1 analogs by PAD2

| | -6 D | -5 S | -4 Q | -3 F | -2 A | -1 F | R | 1 G | 2 A | 3 S | 4 A | 5 S | 6 D |
|---|---|---|---|---|---|---|---|---|---|---|---|---|---|
| H | | | 200 | 195 | 210 | 150 | | 225 | 200 | 210 | 200 | | |
| I | | | 175 | 95 | 185 | 45 | | 175 | 140 | 225 | 140 | | |
| K | | | 215 | 210 | 220 | 100 | | 190 | 220 | 240 | 215 | | |
| L | | | 170 | 95 | 210 | 100 | | 175 | 165 | 210 | 140 | | |
| M | | | 190 | 115 | 185 | 100 | | 150 | 185 | 175 | 150 | | |
| N | | | 165 | 95 | 165 | 50 | | 225 | 115 | 80 | 150 | | |
| P | | | 170 | 30 | 115 | 5 | | 15 | 70 | 130 | 140 | | |
| Q | | | 100 | 80 | 185 | 25 | | 125 | 140 | 65 | 150 | | |
| R | | | 115 | 260 | 185 | 175 | | 225 | 225 | 290 | 225 | | |
| S | | | 150 | 30 | 150 | 25 | | 165 | 165 | 100 | 140 | | |
| T | | | 155 | 50 | 200 | 40 | | 175 | 150 | 145 | 125 | | |
| V | | | 170 | 50 | 185 | 50 | | 190 | 115 | 225 | 125 | | |
| W | | | 210 | 260 | 210 | 115 | | 200 | 200 | 195 | 225 | | |
| Y | | | 185 | 130 | 210 | 125 | | 200 | 185 | 225 | 175 | | |

Based on the above results we designed 15 peptides containing multiple amino acids that improve substrate properties (see Table 9). The indicated peptides were synthesized and tested in order to identify the best substrate from this group.

TABLE 9

| Peptide code | SEQ ID NO: | Sequence | Conversion (%) |
|---|---|---|---|
| 0735-27 | 92 | D-S-K-W-Y-H-R-N-K-F-W-S-D | 98 |
| 0735-28 | 93 | D-S-Q-F-A-H-R-N-A-S-A-S-D | 35 |
| 0735-29 | 94 | D-S-W-K-A-F-R-G-A-S-A-S-D | 70 |
| 0735-30 | 95 | D-S-Q-F-A-F-R-G-A-F-W-S-D | 65 |
| 0735-31 | 96 | D-S-M-C-A-F-R-G-A-K-K-S-D | 59 |
| 0735-32 | 97 | D-S-Q-F-A-F-R-H-F-S-A-S-D | 85 |
| 0735-33 | 98 | D-S-Q-W-A-F-R-G-A-F-A-S-D | 82 |
| 0735-34 | 99 | D-S-K-F-K-F-R-Y-A-Y-A-S-D | 91 |
| 0735-35 | 100 | D-S-K-F-H-F-R-Y-A-V-A-S-D | 92 |
| 0735-36 | 101 | D-S-Q-F-A-Y-R-N-A-K-A-S-D | 74 |
| 0735-37 | 102 | D-S-Q-W-A-F-R-H-A-L-F-S-D | 95 |
| 0735-38 | 103 | D-S-Q-W-A-F-R-N-A-F-A-S-D | 82 |
| 0735-39 | 104 | D-S-Q-F-K-F-R-G-A-F-A-S-D | 80 |
| 0735-40 | 105 | D-S-Q-C-L-F-R-G-A-F-A-S-D | 73 |
| 0735-41 | 106 | D-S-K-F-A-F-R-G-G-I-A-S-D | 90 |
| 0308-29 | 11 | D-S-Q-F-A-F-R-G-A-S-A-S-D | 45 (=L1) |

Peptides of table 9 are represented by the following sequences SEQ ID NO: 92-106 and SEQ ID NO:11 as control (L1).

From these results it is obvious that this set of peptides contains PAD2 substrates with improved substrate properties compared to L1 (0308-29).

In order to obtain optimized peptide substrates for PAD2 and PAD4, 36 of the peptides mentioned in Tables 4, 5, 7 and 9 were selected and tested as substrate for PAD2 and PAD4. Subsequently, the five peptides indicated with ** were selected for further investigation.

TABLE 10

| Peptide code | SEQ ID NO: | Sequence | Conversion by PAD4 (%) | Conversion by PAD2 (%) |
|---|---|---|---|---|
| 0735-27 | 92 | D-S-K-W-Y-H-R-N-K-F-W-S-D | 45 | 98 |
| 0735-34 | 99 | D-S-K-F-K-F-R-Y-A-Y-A-S-D | <20 | 91 |
| 0735-35 | 100 | D-S-K-F-H-F-R-Y-A-V-A-S-D | <20 | 92 |
| 0735-37 | 102 | D-S-Q-W-A-F-R-H-A-L-F-S-D | <20 | 95 |
| 0735-41 | 106 | D-S-K-F-A-F-R-G-G-I-A-S-D | 25 | 90 |
| 0608-23 | 24 | D-S-K-H-F-H-R-D-F-I-Y-S-D | 69 | 94 |
| 0608-24 | 25 | D-S-K-H-L-S-R-E-W-M-W-S-D | 54 | 95 |
| 0608-27 | 28 | D-S-K-H-K-S-R-D-F-V-Y-S-D | 69 | 94 |
| 0608-29 | 30 | D-S-K-K-L-H-R-D-H-M-E-S-D | 65 | 90 |

TABLE 10-continued

| Peptide code | SEQ ID NO: | Sequence | Conversion by PAD4 (%) | Conversion by PAD2 (%) |
|---|---|---|---|---|
| 0608-32 | 33 | D-S-K-K-H-R-E-W-V-W-S-D | 72 | 100 |
| 0608-35 | 36 | D-S-H-K-W-H-R-D-F-F-Y-S-D | 73 | 92 |
| 0608-36 | 37 | D-S-H-K-H-S-R-E-W-L-W-S-D | 51 | 97 |
| 0608-43 | 44 | D-S-H-K-F-D-R-D-F-I-Y-S-D | 79 | 90 ** |
| 0708-15 | 72 | D-S-K-K-F-D-R-D-H-L-Y-S-D | 77 | 90 |
| 0708-18 | 75 | D-S-K-W-H-H-R-D-H-L-Y-S-D | 71 | 90 |
| 0708-20 | 77 | D-S-K-K-H-D-R-D-H-L-W-S-D | 80 | 95 |
| 0708-22 | 79 | D-S-K-K-H-F-R-D-K-L-Y-S-D | 37 | 92 |
| 0708-25 | 82 | D-S-K-K-F-H-R-D-F-L-Y-S-D | 64 | 97 |
| 0708-26 | 83 | D-S-K-K-F-K-R-D-F-L-F-S-D | 35 | 97 |
| 0708-29 | 86 | D-S-K-K-Y-D-R-D-F-L-W-S-D | 76 | 92 |
| 0708-30 | 87 | D-S-K-K-F-D-R-G-H-L-Y-S-D | 80 | 90 |
| 0708-31 | 88 | D-S-K-W-H-H-R-G-H-L-Y-S-D | 71 | 96 |
| 0708-32 | 89 | D-S-K-K-H-F-R-G-K-L-Y-S-D | 22 | 96 |
| 0708-33 | 90 | D-S-K-K-F-H-R-G-F-L-Y-S-D | 73 | 100 |
| 0708-34 | 91 | D-S-K-K-Y-D-R-G-F-L-W-S-D | 81 | 93 |
| 0612-26 | 50 | F-F-D-S-K-H-L-S-R-E-W-M-W-S-D | 73 | 97 |
| 0612-29 | 53 | F-F-D-S-K-H-K-S-R-D-F-V-Y-S-D | 77 | 92 |
| 0612-30 | 54 | F-F-D-S-K-H-F-D-R-E-W-I-W-S-D | 89 | 94 ** |
| 0612-32 | 56 | F-F-D-S-K-K-W-S-R-E-Y-F-F-S-D | 76 | 94 |
| 0612-34 | 58 | F-F-D-S-K-K-H-R-E-W-V-W-S-D | 76 | 99 |
| 0612-35 | 59 | F-F-D-S-K-K-F-S-R-D-H-I-E-S-D | 63 | 90 |
| 0612-37 | 61 | F-F-D-S-H-K-W-H-R-D-F-F-Y-S-D | 88 | 96 ** |
| 0612-38 | 62 | F-F-D-S-H-K-H-S-R-E-W-L-W-S-D | 72 | 96 |
| 0612-44 | 68 | F-F-D-S-H-K-K-S-R-E-Y-V-F-S-D | 58 | 100 |
| 0612-45 | 69 | F-F-D-S-H-K-F-D-R-D-F-I-Y-S-D | 94 | 97 ** |
| 0612-46 | 70 | F-F-D-S-H-K-L-H-R-E-W-M-W-S-D | 91 | 92 ** |
| 0308-29 | 11 | D-S-Q-F-A-F-R-G-A-S-A-S-D | <20(=L1) | <20(=L1) |
| 0608-31 | 32 | D-S-K-K-H-D-R-D-F-L-Y-S-D | 58(=L2) | 84(=L2) |

Based on the sequence of the five indicated peptides and that of L2, PAD inhibitors were generated and tested. The inhibitors were generated in such a way that the R in the substrate sequence was replaced by ornithine carrying an electrophilic trap or group (either a fluoroamidine or a chloroamidine). In addition, we modified the N-terminus with an acetyl group (Ac) and the C-terminus as an amide in order to increase stability of the inhibitors. See Tables 11 and 12.

TABLE 11

| Peptide code | SEQ ID NO: | Sequence | Code of corresponding substrate |
|---|---|---|---|
| 0741-01FA | 107 | Ac-F-F-D-S-K-H-F-D-O(FA)-E-W-I-W-S-D-amide | 0612-30 |
| 0741-01FA | 108 | Ac-F-F-D-S-H-K-W-H-O(FA)-D-F-F-Y-S-D-amide | 0612-37 |

TABLE 11-continued

| Peptide code | SEQ ID NO: | Sequence | Code of corresponding substrate |
|---|---|---|---|
| 0741-01FA | 109 | Ac-F-F-D-S-H-K-F-D-O(FA)-D-F-I-Y-S-D-amide | 0612-45 |
| 0741-01FA | 110 | Ac-F-F-D-S-H-K-L-H-O(FA)-E-W-M-W-S-D-amide | 0612-46 |
| 0741-01FA | 111 | Ac-D-S-H-K-F-D-O(FA)-D-F-I-Y-S-D-amide | 0608-43 |
| 0741-01FA | 112 | Ac-D-S-K-K-H-D-O(FA)-D-F-L-Y-S-D-amide | 0608-31 (=L2) |

O(FA) = Orn(fluoro-amidine

TABLE 12

| Peptide code | SEQ ID NO: | Sequence | Code of corresponding substrate |
|---|---|---|---|
| 0741-01CA | 113 | Ac-F-F-D-S-K-H-F-D-O(CA)-E-W-I-W-S-D-amide | 0612-30 |
| 0741-01CA | 114 | Ac-F-F-D-S-H-K-W-H-O(CA)-D-F-F-Y-S-D-amide | 0612-37 |
| 0741-01CA | 115 | Ac-F-F-D-S-H-K-F-D-O(cA)-D-F-I-Y-S-D-amide | 0612-45 |
| 0741-01CA | 116 | Ac-F-F-D-S-H-K-L-H-O(CA)-E-W-M-W-S-D-amide | 0612-46 |
| 0741-01CA | 117 | Ac-D-S-H-K-F-D-O(CA)-D-F-I-Y-S-D-amide | 0608-43 |
| 0741-01CA | 118 | Ac-D-S-K-K-H-D-O(CA)-D-F-L-Y-S-D-amide | 0608-31 (=L2) |

O(CA) = Orn(chloro-amidine

The above inhibitors were tested for their inhibitory capacity on PAD2 and PAD4. In short, various concentrations of the inhibitor were mixed with a constant concentration of substrate (peptide 0708-30). Subsequently, PAD was added and after incubation the conversion of the substrate was determined. Thus, the lower the conversion, the better the inhibitor. Results are depicted in Table 13 and 14.

TABLE 13 conversion of 0708-30 by PAD2 in the presence of various inhibitors

| Peptide code | SEQ ID NO: | Concentration of inhibitor | | |
|---|---|---|---|---|
| | | 100 µM | 50 µM | 10 µM |
| 0741-01FA | 107 | 14 | 29 | 69 |
| 0741-02FA | 108 | 7 | 17 | 52 |
| 0741-03FA | 109 | 6 | 13 | 39 |
| 0741-04FA | 110 | 14 | 24 | 62 |
| 0741-05FA | 111 | 15 | 24 | 54 |
| 0741-06FA | 112 | 25 | 42 | 73 |
| 0741-01CA | 113 | 23 | 38 | 69 |
| 0741-02CA | 114 | 18 | 32 | 67 |
| 0741-03CA | 115 | 23 | 49 | 57 |
| 0741-04CA | 116 | 50 | 47 | 69 |
| 0741-05CA | 117 | 31 | 44 | 62 |
| 0741-06CA | 118 | 48 | 45 | 63 |

TABLE 14 conversion of 0708-30 by PAD4 in the presence of various inhibitors

| Peptide code | SEQ ID NO: | Concentration of inhibitor | | |
|---|---|---|---|---|
| | | 100 µM | 50 µM | 10 µM |
| 0741-01FA | 107 | 15 | 24 | 63 |
| 0741-02FA | 108 | 16 | 20 | 50 |
| 0741-03FA | 109 | 9 | 12 | 45 |
| 0741-04FA | 110 | 14 | 28 | 64 |
| 0741-05FA | 111 | 14 | 22 | 55 |
| 0741-06FA | 112 | 27 | 43 | 74 |
| 0741-01CA | 113 | 17 | 31 | 63 |
| 0741-02CA | 114 | 19 | 31 | 63 |
| 0741-03CA | 115 | 14 | 24 | 62 |
| 0741-04CA | 116 | 26 | 55 | 68 |
| 0741-05CA | 117 | 25 | 34 | 74 |
| 0741-06CA | 118 | 50 | 64 | 74 |

The results from Tables 13 and 14 indicate that in this group inhibitors containing O(FA) are more effective in inhibiting PAD2 and PAD4 compared to their counterparts containing O(CA).

In order to investigate whether peptide length is crucial for the inhibitory activity of the peptides, the peptides were also generated and tested as the corresponding 7-mers from the middle part of the inhibitors. See Table 15.

TABLE 15

| Peptide code | SEQ ID NO: | Sequence |
|---|---|---|
| 0748-01FA | 119 | Ac-H-F-D-O(FA)-E-W-I-amide |
| 0748-09FA | 120 | Ac-K-W-H-O(FA)-D-F-F-amide |

TABLE 15-continued

| Peptide code | SEQ ID NO: | Sequence |
|---|---|---|
| 0748-17FA | 121 | Ac-K-L-H-O(FA)-E-W-M-amide |
| 0743-58FA | 122 | Ac-K-F-D-O(FA)-D-F-I-amide |
| 0748-25FA | 123 | Ac-K-H-D-O(FA)-D-F-L-amide |

O(FA) = Orn(fluoro-amidine)

These shortened variants were tested as inhibitors for PAD2 and PAD 4 as described above. Results are depicted in Tables 16 and 17.

TABLE 16 conversion of 0708-30 by PAD2 in the presence of various inhibitors

| | | Concentration of inhibitor | | | |
|---|---|---|---|---|---|
| Peptide code | SEQ ID NO: | 100 µM | 50 µM | 10 µM | 0 µM |
| 0748-01FA | 119 | 21 | 36 | 67 | 68 |
| 0748-09FA | 120 | 5 | 6 | 23 | 68 |
| 0748-17FA | 121 | 24 | 35 | 58 | 68 |
| 0743-58FA | 122 | 4 | 8 | 33 | 68 |
| 0748-25FA | 123 | 11 | 20 | 47 | 68 |

TABLE 17 conversion of 0708-30 by PAD4 in the presence of various inhibitors

| | | Concentration of inhibitor | | | |
|---|---|---|---|---|---|
| Peptide code | SEQ ID NO: | 100 µM | 50 µM | 10 µM | 0 µM |
| 0748-01FA | 119 | 12 | 25 | 50 | 81 |
| 0748-09FA | 120 | 13 | 22 | 51 | 81 |
| 0748-17FA | 121 | 18 | 32 | 64 | 81 |
| 0743-58FA | 122 | 10 | 19 | 38 | 81 |
| 0748-25FA | 123 | 12 | 18 | 45 | 81 |

These results indicate that 7-mer inhibitors can be about equally effective inhibitors for PAD2 and PAD4 compared to e.g. 13-mer and 15-mer peptides.

Example 3

Mechanism of Binding of the Inhibitors to Pad

In the following experiments mixtures of various quantities of biotinylated inhibitor peptide (biotin-Ahx-D-S-K-K-H-D-O(FA)-D-F-L-Y-S-D-amide (SEQ ID NO: 112), O(FA)=ornithine fluoroamidine, Ahx=6-aminohexanoic acid) and a fixed amount of His-tagged PAD4 were analysed. In short, 10 µl PAD4 solution was mixed with 10 µl inhibitor solution and incubated for 3 h at 37° C. After the addition of loading buffer containing SDS, samples were either boiled for 5 minutes or kept at room temperature. Samples were loaded on a 10% polyacrylamide gel and subjected to electrophoresis (about 1 h). Proteins were transferred to a PVDF membrane and developed with either streptavidin-alkaline phosphatase conjugate (FIG. 2) or with mouse-anti-His antibody followed by goat-anti-mouse alkaline phosphatase conjugate (FIG. 3), followed by visualisation using NBT/BCIP. In Table 18 the samples are specified.

TABLE 18

| Lane | Amount of PAD4 | Amount inhibitor | Treatment |
|---|---|---|---|
| 1, 11 | 20 pmol PAD4 | 20,000 pmol | boiled |
| 2, 12 | 20 pmol PAD4 | 2,000 pmol | boiled |
| 3, 13 | 20 pmol PAD4 | 200 pmol | boiled |
| 4, 14 | 20 pmol PAD4 | no inhibitor | boiled |
| 5, 15 | 20 pmol PAD4 | 20,000 pmol | not boiled |
| 6, 16 | 20 pmol PAD4 | 2,000 pmol | not boiled |
| 7, 17 | 20 pmol PAD4 | 200 pmol | not boiled |
| 8, 18 | 20 pmol PAD4 | no inhibitor | not boiled |
| 9, 19 | | 20,000 pmol | not boiled |
| M | Marker mixture | | |

Figure 2:
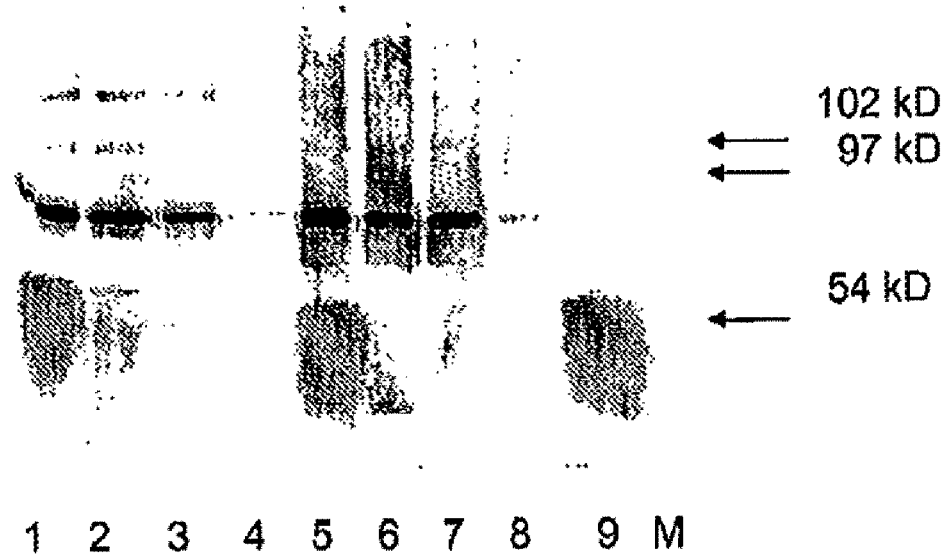
FIG. 2. Blot developed with streptavidin-alkaline phosphatase. Mixtures of various quantities of biotinylated inhibitor peptide (biotin-Ahx-D-S-K-K-H-D-O(FA)-D-F-L-Y-S-D-amide (SEQ ID NO: 112), O(FA)=ornithine fluoroamidine, Ahx=6-aminohexanoic acid) and a fixed amount of His-tagged PAD4 were analysed by SDS-PAGE gel electrophoresis. Proteins were transferred to a PVDF membrane and developed with streptavidine-alkaline phosphatase conjugate, followed by visualisation using NBT/BCIP. In Table 18 the samples are specified.
Figure 3:
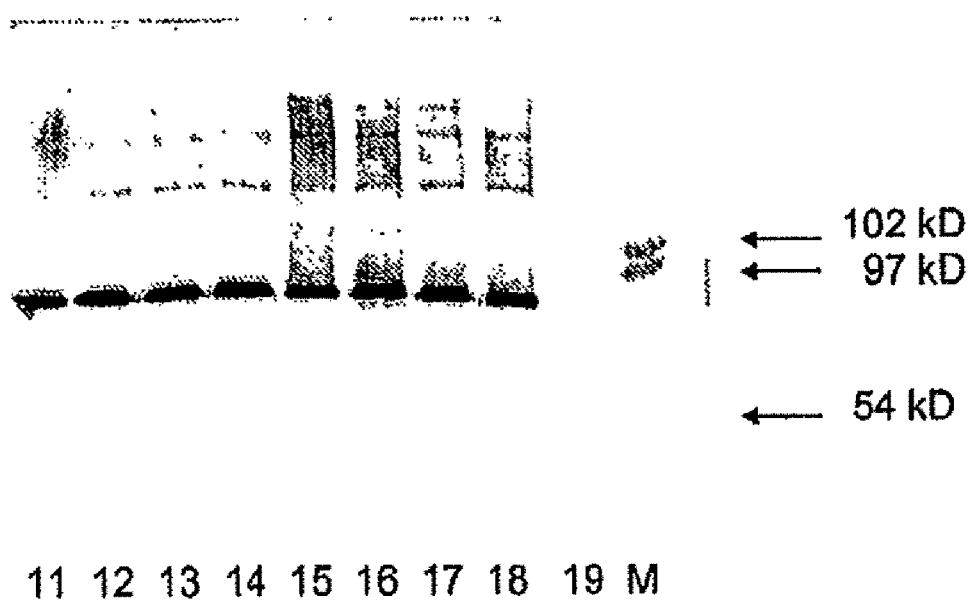
FIG. 3. Blot developed with 1 mouse anti-His, 2 goat anti mouse-alkaline phosphatase. Mixtures of various quantities of biotinylated inhibitor peptide (biotin-Ahx-D-S-K-K-H-D-O(FA)-D-F-L-Y-S-D-amide (SEQ ID NO: 112), O(FA)=ornithine fluoroamidine, Ahx=6-aminohexanoic acid) and a fixed amount of His-Tagged PAD4 were analysed by SDS-PAGE gel electrophoresis. Proteins were transferred to a PVDF membrane and developed with mouse-anti-His antibody followed by goat-anti-mouse alkaline phosphatase conjugate, followed by visualisation using NBT/BCIP. In Table 18 the samples are specified.

In FIG. 2 the biotin group of the inhibitor is visualised. Only lanes where the biotinylated inhibitor is present show a coloured band. The position of the bands is around the expected molecular weight of PAD4 (77 kDa). This indicates binding of the biotinylated peptide to PAD4. This binding is not broken by boiling of the sample in the presence of SDS. In FIG. 3 the His-tag of PAD4 is visualised. Only lanes where PAD4 is present show a coloured band. Lane 19, containing only the inhibitor, doesn't show this band. The position of the bands is around the expected molecular weight of PAD4 (77 kDa) and is at the same position as in FIG. 2, indicating that the bands represent the same molecular weight in both blots. In conclusion, the biotinylated inhibitory peptide was shown to bind to PAD4, and this binding is resistant to boiling of the sample in the presence of SDS, indicating covalent binding of the inhibitor to PAD4.

Example 4

HPLC Assay to Determine Inhibition Pad Activity

With this assay inhibition of PAD activity was determined. The fluorescent substrate Dns-Gly-Arg was used, that is converted into Dns-Gly-Cit by PAD2 or PAD4 (Dns=dansyl). PAD2 or PAD4 was incubated with a mixture containing a fixed concentration of substrate and various concentrations of inhibitor. The above conversion was quantified using HPLC and indicates the effect of the inhibitor.

In short, the reaction mixture (25 µl) containing PAD, the substrate and the inhibitor was incubated at 37° C. Then 125 µl acetic acid/water 15/85 (v/v) was added to quench the conversion. Of this mixture 75 µl was applied to an HPLC equipped with a fluorescence detector. Chromatographic conditions were as follows:
Column: Vydac 218TP5415 $C_{18}$-column. Buffer A: 75 mM sodium acetate and 3.3 mM sodium octanesulfonate in water/acetonitrile 3/1 (v/v), pH 4.0. Buffer B: acetonitrile.
Gradient: t=0 min, 100% A; t=13 min, 100% A; t=15 min, 0% A; t=17 min, 0% A; t=17.5 min, 100% A, t=23 min, 100% A.
Detection: fluorescence Ex 333 nm, Em 533 nm. Flow 0.8 ml/min.

Example 5

ABAP Assay to Determine Inhibition of Pad Activity

To determine inhibition of PAD2 and PAD4 activity, the commercially available Antibody based PAD enzyme activity assay from ModiQuest Research (cat no: MQ17.101) has been used according to manufacturers specifications.

PAD enzymes (amounts that give maximum deimination) were mixed with PAD inhibitors at the following concentrations (4.9, 9.8, 19.5, 39, 78.1, 156, 313, 625, 1250, 2500 and 5000 µM) and pre-incubated for 30 minutes at 37° C. After pre-incubation, mixtures of PAD enzymes and inhibitors were added to the wells for an additional incubation of 75 minutes. After thoroughly washing the 96-well plates with PBS, the conversion of the arginines into citrullines of the coating was measured with the use of a propriety anti-citrulline-antibody, followed by a secondary HRP-labelled antibody recognizing the anti-citrulline antibody. Incubation with both antibodies was performed for 1 h at 37° C. PAD inhibition could then be calculated as $IC_{50}$, the concentration of inhibitor that reduces PAD activity by 50%.

Tables 19 and 20 below summarize the results for inhibition of PAD2 and PAD4 obtained with the first 8 pentapeptide inhibitors and peptide inhibitors from the second round of screening (Example 1).

TABLE 19

First 8 pentapeptides inhibitors tested as inhibitors of PAD2 and PAD4

| SEQ ID NO: | Amino acid sequence of the inhibitors | $IC_{50}$ values (μM) | |
|---|---|---|---|
| | | PAD2 | PAD4 |
| 12 | T D O(FA) G S | 19 | 58 |
| 13 | G D O(FA) S G | 17 | 178 |
| 14 | S S O(FA) D G | 14 | 177 |
| 15 | G S O(FA) D G | 18 | 443 |
| 16 | T D O(CA) G S | 34 | 153 |
| 17 | G D O(CA) S G | 76 | 189 |
| 18 | S S O(CA) D G | 55 | 203 |
| 19 | G S O(CA) D G | 172 | 816 |

TABLE 20

Amino acid sequences of the best inhibitors in the second round of screening

| SEQ ID NO: | Amino acid sequence of the inhibitors | $IC_{50}$ values (μM) | |
|---|---|---|---|
| | | PAD2 | PAD4 |
| 12 | T D O(FA) G S | 49 | 129 |
| 20 | G D O(CA) G S | 38 | 60 |
| 21 | Y D O(CA) G S | 58 | 44 |
| 124 | K F D O(FA) D F I | 17 | 122 |
| 125 | K W H O(FA) D F F | 16 | 161 |

Example 6

Colorimetric Assay to Determine Inhibition of Pad Activity

One of the assays that was used to investigate the inhibition of a PAD by the inhibitors, is the colorimetric assay that has been described previously {Sugawara et al. 1998}. In this assay benzoylarginine ethyl ester (BAEE) is incubated with a purified recombinant PAD enzyme as indicated in a buffer containing 50 mM Tris-HCl, pH 7.6, 10 mM CaCl2, 2 mM dithiothreitol for 3 hours at 37° C. To monitor the conversion of BAEE into benzoylcitrulline ethyl ester, the reaction product is incubated with 1.5 mg/ml DAMO (diacetyl monoxime) and 1.0 mg/ml antipyrine in the presence of 15% sulphuric acid, 12% phosphoric acid and 0.16 mg/ml $FeCl_3$ for 10 minutes at 100° C. After cooling down to room temperature, the absorbance is measured at 450 nm.

TABLE 21

Selected inhibitors tested in this test

| Peptide code | SEQ ID NO: | Sequence |
|---|---|---|
| CXP5.3-014 | — | Bz-O(CA)-amide |
| CXP5.3-015 | — | Bz-O(FA)-amide |
| CXP5-101 | 126 | $MeO_2$C-T-D-O(FA)-G-S-methylester |
| CXP5.2-078 | 127 | Ac-G-D-O(CA)-G-S |
| CXP5.2-081 | 128 | Ac-Y-D-O(CA)-G-S |
| CXP5.2-097 | 129 | Ac-F-D-O(FA)-D-F |
| 0743-58FA | 122 | Ac-K-F-D-O(FA)-D-F-I-amide |
| 0741-03FA | 109 | Ac-F-F-D-S-H-K-F-D-O(FA)-D-F-I-Y-S-D-amide |

Bz = benzoyl,
Ac = acetyl,
O(CA) = Orn(chloroamidine),
O(FA) = Orn(fluoroamidine)

To test the efficacy of the inhibitors (see Table 21) in this assay, a recombinant PAD enzyme as indicated was pre-incubated with various concentrations of inhibitory compounds for 15 minutes at 37° C.

Figure 4A:
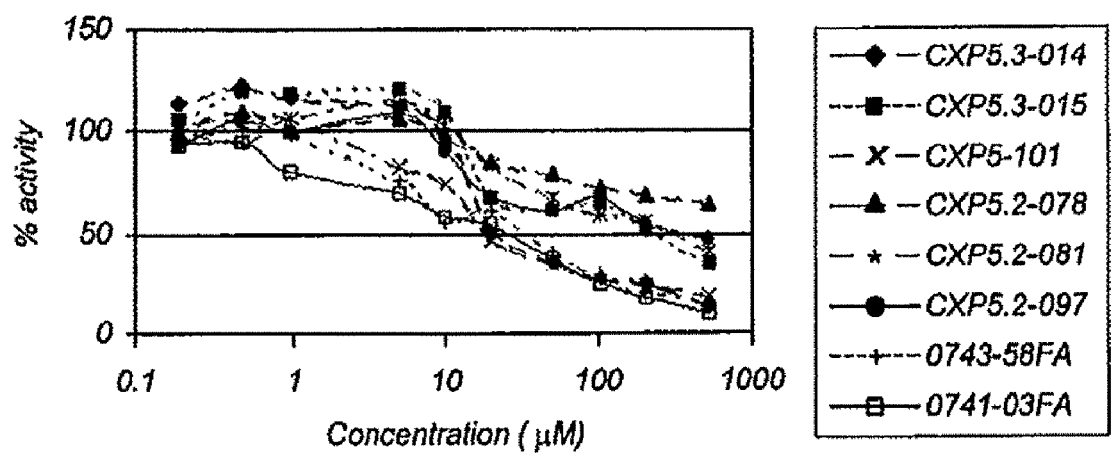
FIG. 4. The capacity of various compounds to inhibit the conversion of benzoylarginine ethyl ester into benzoylcitrulline ethyl ester by a PAD as indicated was determined by the colorimetric assay using DAMO and antipyrine to modify benzoylcitrulline ethyl ester. The conversion of BAEE in the absence of any inhibitory compound was set at 100%.
Figure 4B:
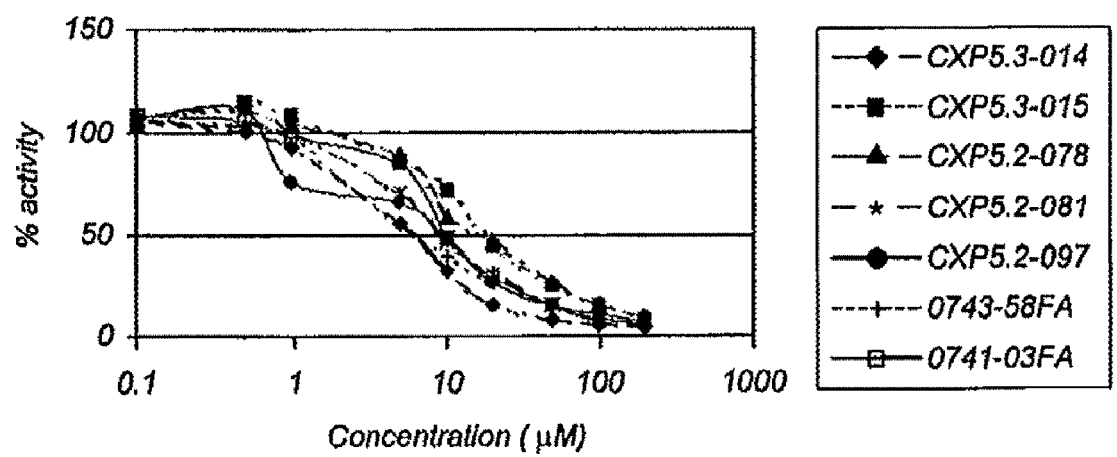

The capacity of various compounds to inhibit the human PAD2 (0.12 μM) and PAD4 (0.2 μM) in this colorimetric assay is illustrated in FIG. 4.

Example 7

Assay to Determine Pad Activity Using Mass Spectrometry

Conversion of arginine into citrulline in the substrate peptides by PAD2 or PAD4 using mass spectrometry was performed as follows. A candidate substrate peptide was incubated with a PAD as indicated for several hours at 37° C. The reaction was quenched by the addition with acetic acid. A sample was analysed on a Qtof mass spectrometer (Micromass, UK) and the mass spectrum was compared with that of the same peptide not treated with PAD. Normally, $2^+$- and $3^+$-ions are detected. The conversion (ΔM=0.98 Da) was calculated on the $2^+$- and $3^+$-ions individually, and subsequently averaged taking into account the relative peak height of the $2^+$- and $3^+$-signals (see FIG. 5).

Example 8

Assays to Determine the Specificity of Inhibitors for Pad 2/4

To monitor the specificity of the inhibitors for PAD enzymes, the compounds were also tested on a series of enzymes that like PAD enzymes contain a cysteine in the active center (or even a Cys-His-Asp triad).

Selected enzymes included the cysteine protease of the peptidase C1 family papain (EC 3.4.22.2), the mammalian cysteine endopeptidase caspase-3 (EC 3.4.22.56), the mammalian calcium dependent protein-glutamine-γ-glutamyl-transferase or transglutaminase (TG) (EC 2.3.2.13), mammalian ATP:creatine N-phosphotransferase or creatine kinase (CK) (EC 2.7.3.2) and finally from the guanidino-group modifying enzymes (GME) human N(G), N(G)-dimethyl-L-arginine dimethylaminohydrolase isotype 1 (hDDAH-1) (EC 3.5.3.18).

The GME superfamily consists of enzymes that catalyze the modification of (methylated) guanidine groups. Members of this superfamily are characterized by the conservation of key catalytic residues and although the particular substrates and products of these enzymes differ, their catalytic mechanisms are proposed to proceed through similar covalent S-alkyl-thiouronium intermediates formed by the nucleophilic attack of the active-site Cys residue {Shirai et al., 2006}. PAD enzymes and hDDAH-1 belong to this superfamily.

Human DDAH-1 catalyzes the hydrolysis of N(G)-methyl-L-arginine (MMA) and asymmetric N(G), N(G)-dimethyl-L-arginine (ADMA) to L-citrulline and either methylamine or dimethylamine respectively.

The most commonly used procedure to determine hDDAH-1 activity relies on diacetyl monoxime (DAMO) derivatization of the ureido group in L-citrulline to form a colored product. This assay has been optimized for monitoring DDAH activity in a 96-well format {Knipp et al., 2000}.

Purified recombinant $His_6$-tagged hDDAH-1 was incubated with its substrate ADMA in assay buffer (100 mM $Na_2HPO_4$, pH 8.0) at 37° C. for 1 h. The reaction was quenched by the addition of 0.3 M trifluoroacetic acid. The L-citrulline formed was modified with 1.5 mg/ml DAMO (diacetyl monoxime) and 1.0 mg/ml antipyrine in the presence of 15% sulphuric acid, 12% phosphoric acid and 0.16 mg/ml FeCla3 for 10 minutes at 100° C. After cooling down to room temperature, the absorbance was measured at 450 nm.

Upon incubation of purified recombinant caspase-3 with its commercially available substrate: acetyl-Asp-Glu-Val-Asp-p-nitroanilide (Ac-DEVDpNA) SEQ ID NO: 145 in CFS buffer (220 mM mannitol, 68 mM sucrose, 2mM NaCl, 2.5 mM $KH_2PO_4$, 10 mM HEPES, pH 7.4 plus a cocktail of protease inhibitors), the substrate is cleaved, pNA is released and its absorbance at 405 nm can be monitored.

The activity of papain was assessed using a similar experimental setting, based on its cleavage of pGlu-Phe-Leu-pNA in reaction buffer (25 mM Tris-HCL, pH 7.6; 150 mM NaCl).

The activities of CK and TG (both purchased from Sigma-Aldrich (Schnelldorf, Germany) were assayed with the help of the commercial kits CK NAC activated liquiUV test form Human GmbH (Wiesbaden, Germany) and the Enzymatic Assay of TRANSGLUTAMINASE from Sigma-Aldrich (Schnelldorf, Germany) according to the manufacturers' instructions.

Typically the inhibitory properties of the compounds were assessed by treating the enzymes with various concentrations of inhibitors (50 µM to 2.5 mM) for 10 min at room temperature before assaying for activity. The results of these experiments are summarized in Table 22.

TABLE 22

Inhibition of the catalytic activity of various enzymes by PAD inhibitors.

| | $IC_{50}$ values (µM) Inhibitor | | | | |
|---|---|---|---|---|---|
| Enzyme | CXP5-101 | CXP5.2-078 | CXP5.2-081 | 0748-09FA | 0743-58FA |
| hPAD2* | 35 | >500 | 200 | nt** | 35 |
| hPAD4* | 10 | 18 | 10 | nt** | 6 |
| hDDAH-1 | >2000 | 1200 | 1330 | nt** | >2000 |
| Caspase-3 | >1000 | 1000 | >1000 | >1000 | 920 |
| Creatine kinase | 780 | 780 | 1000 | 1000 | 800 |
| Transglutaminase | 600 | 730 | >1000 | >1000 | 1000 |
| Papain | >2000 | 1050 | >2000 | >2000 | >2000 |

*Values were determined with the colorimetric assay described in Example 6.
**The inhibition of hPAD2, hPAD4 and hDDAH-1 by 0748-09FA could not be tested in the colorimetric assay, because this inhibitor is not compatible with the reagents used in this assay.

From Table 22, it is clear that the inhibitors tested show high specificity for PAD2 and PAD4, compared to members of a group enzymes that were selected based on the similarity with PAD enzymes with respect to their active sites.

Example 9

Improved Inhibitors with a Modified N-Terminus and/or Selected D-Amino Acids at the C-terminus The inhibitors described above in example 2 contain an acetyl group on the N-terminus and a C-terminal amide. Although these modifications will protect the inhibitor against the proteolysis by some exopeptidases, it is known that particular exopeptidases are able to hydrolyze acetylated or amidated peptides. In addition, we hypothesized that addition of the small hydrophilic spacer group 2-(2-aminoethoxy)-ethoxy-acetic acid (AEEAc) to the C-terminus of an inhibitor will provide protection against degradation by carboxypeptidases. Based on the sequence of inhibitors 0743-58FA and 0748-09FA described above, we thus synthesized and tested inhibitors that contain either one of these modifications or both. See Table 23.

TABLE 23

Peptide sequences of N- and/or C-terminally modified inhibitors

| Peptide code | SEQ ID NO: | Sequence |
|---|---|---|
| 0743-58FA | 122 | Ac-K-F-D-Orn(FA)-D-F-I-amide |
| 0837-13FA | 130 | Ac-K-F-D-Orn(FA)-D-F-I-X-amide |
| 0837-27FA | 131 | Naf-K-F-D-Orn(FA)-D-F-I-X-amide |
| 0837-29FA | 132 | Naf-K-F-D-Orn(FA)-D-F-I-amide |
| 0748-09FA | 120 | Ac-K-W-H-Orn(FA)-D-F-F-amide |

TABLE 23-continued

Peptide sequences of N- and/or C-terminally modified inhibitors

| Peptide code | SEQ ID NO: | Sequence |
|---|---|---|
| 0837-14FA | 133 | Ac-K-W-H-Orn(FA)-D-F-F-X-amide |
| 0837-28FA | 134 | Naf-K-W-H-Orn(FA)-D-F-F-X-amide |
| 0837-30FA | 135 | Naf-K-W-H-Orn(FA)-D-F-F-amide |

Ac = acetyl,
Naf = 2-naftylsulfonyl,
X = AEEAc

The modified inhibitors were tested on their ability to inhibit PAD 2 (Table 24) or PAD4 (Table 25).

TABLE 24

Inhibition of PAD2

| Peptide code | SEQ ID NO: | Concentration of inhibitor | | | | |
|---|---|---|---|---|---|---|
| | | 80 μM | 40 μM | 20 μM | 10 μM | 0 μM |
| 0743-58FA | 122 | 9 | 15 | 26 | 39 | 74 |
| 0837-13FA | 130 | 11 | 20 | 30 | 43 | 74 |
| 0837-27FA | 131 | 4 | 7 | 14 | 24 | 74 |
| 0837-29FA | 132 | 2 | 5 | 9 | 16 | 74 |
| 0748-09FA | 120 | 4 | 8 | 14 | 25 | 76 |
| 0837-14FA | 133 | 8 | 14 | 24 | 38 | 76 |
| 0837-28FA | 134 | 2 | 4 | 8 | 17 | 76 |
| 0837-30FA | 135 | 1 | 2 | 3 | 9 | 76 |

TABLE 25

Inhibition of PAD4

| Peptide code | SEQ ID NO: | Concentration of inhibitor | | | | |
|---|---|---|---|---|---|---|
| | | 80 μM | 40 μM | 20 μM | 10 μM | 0 μM |
| 0743-58FA | 122 | 13 | 18 | 36 | 46 | 71 |
| 0837-13FA | 130 | 16 | 23 | 33 | 48 | 71 |
| 0837-27FA | 131 | 7 | 12 | 20 | 35 | 71 |
| 0837-29FA | 132 | 5 | 10 | 16 | 33 | 71 |
| 0748-09FA | 120 | 18 | 27 | 38 | 51 | 67 |
| 0837-14FA | 133 | 21 | 29 | 39 | 54 | 67 |
| 0837-28FA | 134 | 9 | 17 | 23 | 37 | 67 |
| 0837-30FA | 135 | 7 | 13 | 24 | 37 | 67 |

Surprisingly, it was noticed that some of the inhibitors, that were designed to possess improved stability against enzymatic degradation, showed improved efficacy as an inhibitor of PAD2 and PAD4. As can be observed from Table 24 and Table 25, addition of a 2-naftylsulfonyl group to the N-terminus increases potency of the inhibitor significantly, whereas addition of an AEEAc group to the C-terminus partly diminishes this effect.

Since the addition of an AEEAc group to the C-terminus of the inhibitors decreases efficacy, we tested some other C-terminal modifications that were based on the introduction of D-amino acids, also known to prevent exopeptidase activity.

Table 26 contains the peptides that were used for PAD2 inhibition, Table 27 contains the results of these experiments. Table 28 contains the peptides that were used for PAD4 inhibition, Table 29 contains the results of these experiments.

TABLE 26

Peptide sequences used to test the effect of the introduction of D-amino acids at the C-terminus of the inhibitors to inhibit PAD2 (lower case = D-amino acid)

| Peptide code | SEQ ID NO: | Sequence |
|---|---|---|
| 0743-58FA | 122 | Ac-K-F-D-Orn(FA)-D-F-I-amide |
| 0838-91FA | 136 | Naf-K-F-D-Orn(FA)-D-F-i-amide |
| 0838-88FA | 137 | Naf-K-F-D-Orn(FA)-D-F-i-y-amide |
| 0838-89FA | 138 | Naf-K-F-D-Orn(FA)-D-F-i-k-amide |
| 0748-09FA | 120 | Ac-K-W-H-Orn(FA)-D-F-F-amide |
| 0838-90FA | 139 | Naf-K-W-H-Orn(FA)-D-F-f-amide |
| 0838-86FA | 140 | Naf-K-W-H-Orn(FA)-D-F-f-y-amide |
| 0838-87FA | 141 | Naf-K-W-H-Orn(FA)-D-F-f-k-amide |

Ac = acetyl,
Naf = 2-naftylsulfonyl

TABLE 27

Inhibition of PAD2

| Peptide code | SEQ ID NO: | Concentration of inhibitor | | | | |
|---|---|---|---|---|---|---|
| | | 80 μM | 40 μM | 20 μM | 10 μM | 0 μM |
| 0743-58FA | 122 | 9 | 15 | 24 | 37 | 72 |
| 0838-91FA | 136 | 4 | 8 | 14 | 26 | 72 |
| 0838-88FA | 137 | 6 | 11 | 21 | 38 | 72 |
| 0838-89FA | 138 | 4 | 8 | 13 | 25 | 72 |
| 0748-09FA | 120 | 4 | 8 | 12 | 22 | 73 |
| 0838-90FA | 139 | 1 | 2 | 3 | 6 | 73 |
| 0838-86FA | 140 | 2 | 3 | 7 | 11 | 73 |
| 0838-87FA | 141 | 2 | 3 | 5 | 8 | 73 |

TABLE 28

Peptide sequences used to test the effect of the introduction of D-amino acids at the C-terminus of the inhibitors to inhibit PAD4 (lower case = D-amino acid)

| Peptide code | SEQ ID NO: | Sequence |
|---|---|---|
| 0837-29FA | 132 | Naf-K-F-D-Orn(FA)-D-F-I-amide |
| 0838-91FA | 136 | Naf-K-F-D-Orn(FA)-D-F-i-amide |
| 0838-88FA | 137 | Naf-K-F-D-Orn(FA)-D-F-i-y-amide |
| 0838-89FA | 138 | Naf-K-F-D-Orn(FA)-D-F-i-k-amide |
| 0837-30FA | 135 | Naf-K-W-H-Orn(FA)-D-F-F-amide |
| 0838-90FA | 139 | Naf-K-W-H-Orn(FA)-D-F-f-amide |
| 0838-86FA | 140 | Naf-K-W-H-Orn(FA)-D-F-f-y-amide |
| 0838-87FA | 141 | Naf-K-W-H-Orn(FA)-D-F-f-k-amide |

Naf = 2-naftylsulfonyl

TABLE 29

Inhibition of PAD4

| Peptide code | Peptide code | Concentration of inhibitor | | | | |
|---|---|---|---|---|---|---|
| | | 80 μM | 40 μM | 20 μM | 10 μM | 0 μM |
| 0837-29FA | 132 | 5 | 9 | 15 | 29 | 69 |
| 0838-91FA | 136 | 5 | 8 | 14 | 25 | 69 |
| 0838-88FA | 137 | 4 | 8 | 14 | 24 | 71 |
| 0838-89FA | 138 | 8 | 13 | 19 | 31 | 71 |
| 0837-30FA | 135 | 6 | 12 | 20 | 37 | 74 |
| 0838-90FA | 139 | 6 | 11 | 18 | 31 | 74 |
| 0838-86FA | 140 | 4 | 10 | 18 | 33 | 67 |
| 0838-87FA | 141 | 10 | 14 | 23 | 40 | 67 |

From the above results it is obvious that the introduction of D-amino acids at the C-terminus of the inhibitors in order to protect the inhibitors against degradation by carboxypeptidases can provide inhibitors in which the inhibitory efficacy is not reduced compared to the C-terminally unmodified inhibitors.

The above provides preferred inhibitors for PAD2 and PAD4 that contain a 2-naphtylsulfonyl group at the N-terminus and selected D-amino acids at the C-terminus.

Example 10

Demonstration of an Inhibitory Effect of Two PAD Inhibitors in an In Vivo Animal Model One of the peptide based human PAD 2 and PAD 4 inhibitors was tested in the commercially available collagen antibody induced arthritis (CAIA) mouse model (Modiquest research B.V., product number 18.101). Experimental procedures were performed according to manufacturers specifications to induce arthritis in mice (World Wide Web (www) modiquestresearch.nl/shop/files/18.101-50MG%20 _2007.08.22.pdf) In short, on day 0 male DBA/J1 mice (5mice/group) of the age of 8 weeks have been injected i.p. with a mix of 8 anti-collagen antibodies (2.8 mg/mouse). On day 3, mice received another i.p. injection containing 25 ug LPS (to stimulate and synchronize the inflammation response).

From day 3 onwards mice of one group received daily i.v. injections with peptide based inhibitor CXP5.7-011) (SEQ ID NO:143 until day 11 with the exception of day 9. Mice of the placebo group received the placebo (20 mM phosphate in PBS) according to the same scheme.

Animals where scored daily for degree of inflammation in their paws. Scoring has been performed per paw according to the Table 30. The arthritis score for an animal is the sum of the four scores for individual paws, thus the maximum arthritis score per animal can be 8.

TABLE 30

| Swelling observed | Score per paw |
|---|---|
| 1-2 Swollen Toes | 0.25 |
| 3-4 Swollen toes | 0.50 |
| Slightly Swollen footpad or ankle | 0.50-0.75 |
| Swollen Footpad or Ankle +/− toes | 1.00 |
| Swollen Toes + slightly swollen footpad | 1.25 |
| Swollen Toes + swollen footpad | 1.5 |
| Swollen Footpad + Swollen Ankle | 2.00 |

Although administration of the inhibitors at this dosage and via this route of administration was not able to completely protect animals from swelling in their paws, this experiment clearly demonstrates the inhibitory potential of the inhibitor in this model (See FIG. 6).

Example 11

Synthetic Procedures for the Generation of the Peptides

All peptides were prepared using the following general procedures:

General Procedure I: Attachment of N-Fmoc-Amino Acids to Rink AM Resin (if Needed)

After swelling with dry DMF (2 ml) for 1 h, the Rink AM resin (150 mg, theoretical 0.68 mmol/g, 0.10 mmol) was washed with DMF (2×2 ml) and treated with 50% piperidine in DMF (2×2 ml) for 15 min. The resin was washed with DMF (4×2 ml) and treated with a solution of Fmoc-protected amino acid (4 equiv, 0.4 mmol), PyBOP (4 equiv, 0.4 mmol) and NMM (4 equiv, 0.4 mmol) in dry DMF (2 ml) at room temperature for 3 h. The resin was washed with DMF (5×2 ml). Finally, the resin was dried in vacuo to give resin-bound N-Fmoc amino acids.

General Procedure IIa: Fmoc Deprotection

The Fmoc-protected resin was suspended in a solution of 20% piperidine in DMF (3×2 ml) and agitated for 3, 10 and 10 min. The resin was washed with DMF (6×2 ml).

General Procedure IIb (Synthesizer): Fmoc Deprotection

A preloaded Tentagel S Ac resin carrying the proper Fmoc-protected amino acid (10 μmol) or Tentagel S AM resin was washed with NMP (3×0.8 ml) and treated with 20% piperidine in NMP (3×3 min, 0.8 ml). The resin was washed with NMP (6×0.8 ml).

General Procedure IIIa: Coupling with PyBOP/NMM

Fmoc-amino acid (4 equiv), PyBOP (4 equiv), and NMM (4 equiv) were dissolved in DMF (2 ml) and added to the resin. The reaction mixture was shaken at room temperature for 90 min and washed with DMF (5×2 ml).

General Procedure IIIb(Synthesizer): Coupling with PyBOP/NMM

To the resin were added Fmoc-amino acid (6 equiv, 0.6 M in NMP), PyBOP (6 equiv, 0.67 M in NMP) and NMM (12 equiv, 33% solution in NMP). The coupling reaction was performed for 90 min with occasional shaking and at the end of the coupling the resin was washed with NMP (6×0.8 ml).

General Procedure IVa: Introduction of the Acetyl End Group

Acetic anhydride (5 equiv) and DIPEA (10 equiv) were dissolved in DMF to give a 0.5 M solution which was added to the resin. The reaction mixture was shaken at room temperature for 2 h and washed with DMF (3×2 ml) and DCM (2×2 ml).

General Procedure IVb (Synthesizer): Introduction of the Acetyl End Group

A normal coupling was performed using acetic acid instead of an Fmoc-amino acid.

General Procedure Va: Mmt Deprotection

The resin was treated with a mixture of DCM, trifluoroethanol, and acetic acid (7:2:1, 2 ml) for 15 min. This procedure was repeated 7 times. Subsequently, the resin was washed with DCM (2×2 ml), DMF (2×2 ml), 10% NMM in DMF (2×2 ml) and DMF (2×2 ml).

General Procedure Vb (Synthesizer): Mmt Deprotection

The resin was treated 4×25 min with 1.5 ml of a mixture of DCM, trifluoroethanol, and acetic acid (7:2:1). Subsequently, the resin was washed with DCM (2×1.5 ml), NMP (2×1.5 ml) and 10% NMM in NMP (2×1.5 ml, 3 min).

General Procedure Vb: Introduction of the Halo-Amidine Moiety

Ethyl 2-chloroacetimidate hydrochloride (5 equiv), and DIPEA (10 equiv) were dissolved in DMF (2 ml) and added to the resin. The reaction mixture was shaken at room temperature for 4 h and washed with DMF (4×2 ml).

General Procedure VIb (Synthesizer): Introduction of the Halo-Amidine Moiety

Ethyl 2-chloroacetimidate hydrochloride (10 equiv) and DIPEA (20 equiv) were dissolved in NMP (0.2 ml) and added to the resin. The reaction was performed during 1 h with occasional shaking. The resin was washed with NMP, DCM and ether.

General Procedure VIIa: Cleavage with Trifluoroacetic Acid.

The resin was treated with a mixture of TFA, water, and triisopropylsilane (95:2.5:2.5, 2 ml) for 2 h at room temperature. The resin was washed with TFA (2×2 ml), the combined filtrates were concentrated under a stream of $N_2$ and co-evaporated with toluene (3×2 ml). The crude product was precipitated from a mixture of MeOH and $Et_2O$ to yield the product as an off-white solid.

General Procedure VIIb Peptide (Obtained from Synthesizer): Cleavage with Trifluoroacetic Acid.

The resin was treated for 2.5 h with 1 ml TFA containing 5% water. In case W was present in the peptide, 5% triethylsilane was also added to the cleavage mixture. The peptide was precipitated with 9 ml ether/pentane 1/1 and isolated by centrifugation.

The precipitate was isolated, dissolved in water or water/acetic acid and lyophilized to a white solid.

Synthesis of Fmoc-Orn(Mmt)—OH.DIPEA

To a suspension of Fmoc-Orn-OH.HCl (5 g, 12.79 mmol) in DCM (300 ml) was added chlorotrimethylsilane (5.07 ml, 39.7 mmol). The mixture heated to reflux and stirred for 1 h. After cooling the reaction to 0° C., DIPEA (12.26 ml, 70.4 mmol) was slowly added and the mixture was allow to warm to room temperature over a period of 1 h. Mmt-Cl (4.35 g, 14.07 mmol) was added and the orange solution was stirred for 4.5 h. Then, MeOH (85 ml) was added and the reaction was heated to 40° C. for 20 min. The bright yellow solution was washed with brine/$H_2O$ (2:1, 2×200 ml). The aqueous phase was extracted with DCM (150 ml) and the combined organic phases were dried over $Na_2SO_4$ and concentrated in vacuo. Purification by silica gel flash column chromatography (using EtOAc: toluene: MeOH:DIPEA=10:10:3:0.2 followed by EtOAc:toluene:MeOH:DIPEA=10:10:4:0.2 as eluent) followed by co-evaporation with DCM (3×100 ml) yielded the product as a white solid (8.66 g, 90%).

Synthesis of ethyl 2-chloroacetimidate hydrochloride

This compound was synthesized according to the procedures described by Stillings et al. {Stillings, 1986}.

Synthesis of ethyl 2-fluoroacetimidate hydrochloride

This compound was synthesized according to the procedures described by Hughes et al. {Hughes, 1990}

References

1. Arita K, Hashimoto H, Shimizu T, Nakashima K, Yamada M, Sato M (2004): Structural basis for Ca(2+)-induced activation of human PAD4. Nat Struct Mol Biol 11:777-783.
2. Beniac D R, Wood D D, Palaniyar N, Ottensmeyer F P, Moscarello M A, Harauz G (2000): Cryoelectron microscopy of protein-lipid complexes of human myelin basic protein charge isomers differing in degree of citrullination. J Struct Biol 129: 80-95.
3. Boggs J M, Rangaraj G, Koshy K M, Ackerley C, Wood D D, Moscarello M A (1999): Highly deiminated isoform of myelin basic protein from multiple sclerosis brain causes fragmentation of lipid vesicles. J Neurosci Res 57: 529-535.
4. Cambridge G, Leandro M J, Edwards J C, Ehrenstein M R, Salden M, Bodman-Smith M D, Webster A D (2003): Serologic changes following B lymphocyte depletion therapy for rheumatoid arthritis. Arthritis Rheum 48: 2146-2154.
5. Cao L, Goodin R, Wood D, Moscarello M A, Whitaker I N (1999): Rapid release and unusual stability of immunodominant peptide 45-89 from citrullinated myelin basic protein. Biochemistry 38: 6157-6163.
6. Chapuy-Regaud S, Sebbag M, Baeten D, Clavel C, de Keyser F, Serre G (2004): The presence of deiminated fibrin in the synovial membrane is not specific for rheumatoid arthritis. Arthritis Res Ther 6[Suppl 1], S8.
7. Chavanas S, Mechin M C, Takahara H, Kawada A, Nachat R, Serre G, Simon M (2004): Comparative analysis of the mouse and human peptidylarginine deiminase gene clusters reveals highly conserved non-coding segments and a new human gene, PADI6. Gene 330:19-27.
8. Hill J A, Southwood S, Sette A, Jevnikar A M, Bell D A, Cairns E (2003): Cutting Edge: The conversion of arginine to citrulline allows for a high-affinity peptide interaction with the rheumatoid arthritis-associated HLA-DRB1*0401 MHC class II molecule. J. Immunol. 171: 538-541.
9. Ishida-Yamamoto A, Senshu T, Takahashi H, Akiyama K, Nomura K, Iizuka H (2000): Decreased deiminated keratin K1 in psoriatic hyperproliferative epidermis. J Invest Dermatol 114: 701-705
10. Masson-Bessière C, Sebbag M, Durieux J J, Nogueira L, Vincent C, Girbal-Neuhauser E, Durroux R, Cantagrel A, Serre G (2000): In the rheumatoid pannus, anti-filaggrin autoantibodies are produced by local plasma cells and constitute a higher proportion of IgG than in synovial fluid and serum. Clin Exp Immunol 119: 544-552.
11. Masson-Bessière C, Sebbag M, Girbal-Neuhauser E, Nogueira L, Vincent C, Senshu T, Serre G (2001): The major synovial targets of the rheumatoid arthritis-specific antifilaggrin autoantibodies are deiminated forms of the alpha- and beta-chains of fibrin. J Immunol 166: 4177-4184.
12. Moscarello M A, Pritzker L, Mastronardi F G, Wood D D (2002): Peptidylarginine deiminase: a candidate factor in demyelinating disease. J Neurochem 81: 335-343.
13. Moscarello M A, Mak B, Nguyen T A, Wood D D, Mastronardi F G, Ludwin S K (2002): Paclitaxel (Taxol) attenuates clinical disease in a spontaneously demyelinating transgenic mouse and induces remyelination. Mult Scler 8: 130138.
14. Nakashima K, Hagiwara T, Yamada M (2002): Nuclear localization of peptidylarginine deiminase V and histone deimination in granulocytes. J Biol Chem, 277: 49562-49568.
15. Nijenhuis S, Zendman A J, Vossenaar E R, Pruijn G J M, van Venrooij W J (2004): Autoantibodies to citrullinated proteins in rheumatoid arthritis: clinical performance and biochemical aspects of an RA-specific marker. Clin Chim Acta 350: 17-34.

16. O'Connor P W, Lee L, Moscarello M A, Hunter W, Narayana P A & Wolinsky J S (1999): A phase I study of micellar paclitaxel in the treatment of secondary progressive multiple sclerosis [abstract]. Ann Neurol 46: 470.
17. Pritzker L B, Moscarello M A (1998): A novel microtubule independent effect of paclitaxel: the inhibition of peptidylarginine deiminase from bovine brain. Biochim Biophys Acta 1388: 154-160.
18. Pritzker L B, Joshi S, Gowan J J, Harauz G & Moscarello M A (2000): Deimination of myelin basic protein. 1. Effect of deimination of arginyl residues of myelin basic protein on its structure and susceptibility to digestion by cathepsin D. Biochemistry 39: 5374-5381.
19. Ren Y, Tang J, Mok M Y, Chan A W, Wu A, Lau, C S (2003): Increased apoptotic neutrophils and macrophages and impaired macrophage phagocytic clearance of apoptotic neutrophils in systemic lupus erythematosus. Arthritis Rheum 48: 2888-2897.
20. Reparon-Schuijt C C, van Esch W J, van Kooten C, Sctiellekens G A, de Jong B A, van Venrooij W J, Breedveld F C, Verweij C L (2001): Secretion of anti-citrulline-containing peptide antibody by B lymphocytes in rheumatoid arthritis. Arthritis Rheum 44: 41-47.
21. Shirai H, Blundell T L, Mizuguchi K (2001): A novel superfamily of enzymes that catalyze the modification of guanidino groups. Trends Biochem Sci 26: 465-468.
22. Vossenaar E R, Nijenhuis S, Helsen M M, van der Heijden A, Senshu T, van den Berg W B, van Venrooij W J, Joosten L A (2003a): Citrullination of synovial proteins in murine models of rheumatoid arthritis. Arthritis Rheum 48: 2489-2500.
23. Vossenaar E R, van Venrooij W J (2004): Citrullinated proteins: the sparks that may ignite the fire in rheumatoid arthritis. Arthritis Res Ther 6: 107-111.
24. Vossenaar E R, Zendman A J W, van Venrooij W J, Pruijn, G J M (2003b): PAD, a growing family of citrullinating enzymes: Genes, features and involvement in disease. Bioessays 25: 1106-1118.
25. Wood D D, Moscarello M A (1989): The isolation, characterization, and lipid-aggregating properties of a citrulline containing myelin basic protein. J Biol Chem 264: 5121-5127.
26. Wood D, Bilbao J M, O'Connors P, Moscarello M A (1996): Acute multiple sclerosis (Marburg type) is associated with developmentally immature myelin basic protein. Ann Neurol 40: 18-24
27. Petkova S B, Konstantinov K N, Sproule T J, Lyons B L, Awwami M A, Roopenian D C (2006): Human antibodies induce arthritis in mice deficient in the low-affinity inhibitory IgG receptor Fc gamma RIIB. J Exp Med 203: 275-80.
28. Kuhn K A, Kulik L, Tomooka B, Braschler K J, Arend W P, Robinson W H, Holers V M (2006): Antibodies against citrullinated proteins enhance tissue injury in experimental autoimmune arthritis. J Clin Invest 116: 961-73.
29. Hill J A, Bell D A, Brintnell W, Yue D, Wehrli B, Jevnikar A M, Lee D M, Hueber W, Robinson W H, Cairns E (2008): Arthritis induced by posttranslationally modified (citrullinated) fibrinogen in D R4-IE transgenic mice. J Exp Med 205: 967-79.
30. Matsuo K, Xiang Y, Nakamura H, Masuko K, Yudoh K, Noyori K, Nishioka K, Saito T, Kato T (2006): Identification of novel citrullinated autoantigens of synovium in rheumatoid arthritis using a proteomic approach. Arthritis Res Ther 8: R175.
31. Senshu T, Sato T, Inoue T, Akiyama K, Asaga H (1992): Detection of citrulline residues in deiminated proteins on polyvinylidene difluoride membrane, Anal Biochem 203: 94-100.
32. Raats J M, Wijnen E M, Pruijn G J, van den Hoogen F H, van Venrooij W J (2003): Recombinant human monoclonal autoantibodies specific for citrulline-containing peptides from phage display libraries derived from patients with rheumatoid arthritis, J Rheumatol 30: 1696-1711.
33. Zendman A J W, Raijmakers R, Nijenhuis S, Vossenaar E R, van der Tillaart M, Chirivi G S, Raats J M H, van Venrooij W J, Drijfhout J W, Pruijn G J M (2007): ABAP: Antibody-based assay for peptidylarginine deiminases activity, Anal Biochem 369: 232-240.
34. (Luo Y, Arita K, Bhatia M, Knuckley B, Lee Y—H, Stallcup M R, Sato M, Thompson P R (2006): Inhibitors and inactivators of protein arginine deiminase 4: functional and structural characterization, Biochemistry 45: 11727-11736.
35. Sugawara K, Yoshizawa Y, Tzeng S, Epstein W L, Fukuyama K (1998): Colorimetric determination of citrulline residues in proteins, Anal Biochem 265: 92-96.
36. Shirai H, Mokrab Y, Mizuguchi K (2006): The guanidino-group modifying enzymes: structural basis for their diversity and commonality, Proteins 64: 1010-1032.
37. Knipp M, Vašák M (2000): A 96-well microtiter plate assay for the determination of enzymatically formed citrulline, Anal Biochem 286: 257-264.
38. Stillings M R, Welbourn A P, Walter D S (1986): Substituted 1,3,4-thiadiazoles with anticonvulsant activity. 2. Aminoalkyl derivatives, J Med Chem 29: 2280-2284.
39. Hughes L R, Jackman A L, Oldfield J, Smith R C, Burrows K D, Marsham P R, Bishop J A M, Jones T R, O'Connor B M, Calvert A H (1990): Quinazoline antifolate thymidylate synthase inhibitors: alkyl, substituted alkyl, and aryl substituents in the C-2 position, J Med Chem 33: 3060-3067.

The invention claimed is:

1. A compound capable of inhibiting the activity of a PAD comprising a peptide part and a thiol-reactive electrophilic group carried by an amino acid Ω wherein:
   (a) the peptide part comprises at least about 5 amino acids and no more than about 20 amino acids,
   (b) the peptide comprises at least one of the motifs (b1), (b2), (b3) or (b4):
   (b1) G/S/T-D/S-Ω-D/G/S-G/S
   (b2) H/K/F/L/W-S/D/H-Ω-D/E-H/Y/F/W
   (b3) Y/A/K/H/L-F/Y/H-Ω-N/G/H/Y-K/A/F
   (b4) Y-D/S-Ω-D/G/S-G/S
   in which Ω represents an amino acid carrying a thiol-reactive electrophilic group;
   (c) optionally the N-terminus and/or C-terminus of the peptide sequence are modified; and wherein the thiol-reactive electrophilic group is an halogeno-amidine group.

2. A compound according to claim 1, wherein Ω is ornithine.

3. A compound according to claim 1, wherein the motif of (b1) comprises: G/S/T-D-Ω-D-G/S and the motif of (b2) comprises: H/K/F/L/W-D-Ω-D-H/Y/F/W.

4. A compound according to claim 1, wherein the motif is (b4).

5. A compound according to claim 1, wherein the peptide sequence comprises or consists of 7 amino acids.

6. A compound according to claim 1, wherein the N-terminus of the peptide sequence is modified by an acetyl group and/or the C-terminus as an amide.

7. A compound according to claim 1, wherein the N-terminus of the peptide sequence is modified by addition of a 2-naphtylsulfonyl group and/or optionally wherein the C-terminus is modified by addition of a D-amino acid.

8. A compound according to claim 1, wherein the peptide sequence comprises or consists of a sequence selected from the group consisting of SEQ ID NO: 47-71 and 92-106 wherein arginine has been replaced by Ω.

9. A compound according to claim 1, wherein the peptide sequence comprises or consists of a sequence selected from of the group consisting of: SEQ ID NO: 12-21 and 107-143.

10. A compound according to claim 1, wherein the peptide sequence comprises or consists of: a sequence selected from the group consisting of SEQ ID NO: 128-135.

11. A composition comprising a compound as defined in claim 1 and at least one excipient, wherein the composition is suitable for local administration.

12. A composition according to claim 11 further comprising an immunosuppressant and/or an inflammation suppressant agent.

13. A compound according to claim 1, wherein the compound delays and/or treats an autoimmune disorder.

14. A method of treating an autoimmune disorder in a subject with an autoimmune disorder, comprising administering an effective amount of the compound of claim 1, thereby treating the autoimmune disorder.

15. The method of claim 14, wherein the autoimmune disorder is RA.

16. The method of claim 14, wherein administration is by injection.

17. The method of claim 16, wherein administration is intraperitoneal and/or intravenous injection.

18. The method of claim 14, wherein the administration step is repeated at least once.

19. The method of claim 14, further comprising a step of determining inhibition of PAD activity.

20. The method of claim 14, further comprising a step of determining the level of inflammation in a patient before the administration step and after the administration step.

21. The method of claim 14, further comprising a step of identifying a subject in need of treatment.

22. A compound according to claim 9, wherein the peptide sequence comprises or consists of a sequence selected from the group consisting of SEQ ID NO: 20-21, 120, 122 and 127-143.

23. A compound according to claim 22, wherein the peptide sequence comprises or consists of a sequence selected from the group consisting of: SEQ ID NO: 20, 21, 127, 128 and 136-143.

24. A compound according to claim 23, wherein the peptide sequence comprises or consists of a sequence selected from the group consisting of: SEQ ID NO: 138, 141, 142 and 143.

25. A compound according to claim 13, wherein the autoimmune disorder is RA.

26. The composition of claim 11, wherein local administration is injection in a joint or topical transdermal administration.

27. The compound of claim 1, wherein the halogeno-amidine group is fluoroamidine.

28. The compound of claim 1, wherein the halogeno-amidine group is chloroamidine.

* * * * *

SEQUENCE LISTING

```
<160> NUMBER OF SEQ ID NOS: 145

<210> SEQ ID NO 1
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 1

Asp Asp Tyr Ser Ser Ser Arg Asp Gly Tyr Gly Gly Ser
1               5                   10
```

```
<210> SEQ ID NO 2
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 2

Gly Gly Tyr Ser Gly Asp Arg Ser Gly Gly Tyr Gly
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 3

Asp Gly Tyr Gly Gly Ser Arg Asp Ser Tyr Ser Ser Ser
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 4

Asp Ser Tyr Arg Ser Trp Arg Asp Gly Tyr Tyr Ser Asp
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 5

Ile Glu Ile Met Thr Asp Arg Gly Ser Gly Lys Lys Arg
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 6

Ile Gly Ser Arg Gly Asp Arg Ser Gly Phe Gly Lys Phe
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 7

Ile Glu Ile Ile Thr Asp Arg Gln Ser Gly Lys Lys Arg
1               5                   10

<210> SEQ ID NO 8
```

```
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 8

Asp Ser Glu Gly Thr Trp Arg Lys Gly Pro Glu Ala Asp
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 9

Asp Ser Ser Glu Glu Leu Arg Gly Gly Gly Lys Ser Asp
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 10

Asp Ser Arg Phe Tyr Trp Arg Gly Gly Gly Lys Ser Asp
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 11

Asp Ser Gln Phe Ala Phe Arg Gly Ala Ser Ala Ser Asp
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for ornithine fluoroamidine

<400> SEQUENCE: 12

Thr Asp Xaa Gly Ser
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for Ornithine fluoroamidine

<400> SEQUENCE: 13
```

```
Gly Asp Xaa Ser Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for ornithine fluoroamidine

<400> SEQUENCE: 14

Ser Ser Xaa Asp Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for ornithine fluoroamidine

<400> SEQUENCE: 15

Gly Ser Xaa Asp Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for ornithine chloroamidine

<400> SEQUENCE: 16

Thr Asp Xaa Gly Ser
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for ornithine chloroamidine

<400> SEQUENCE: 17

Gly Asp Xaa Ser Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (3)..(3)
<223> OTHER INFORMATION: Xaa stands for ornithine chloroamidine

<400> SEQUENCE: 18

Ser Ser Xaa Asp Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for ornithine chloroamidine

<400> SEQUENCE: 19

Gly Ser Xaa Asp Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for ornithine chloroamidine

<400> SEQUENCE: 20

Gly Asp Xaa Gly Ser
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for ornithine chloroamidine

<400> SEQUENCE: 21

Tyr Asp Xaa Gly Ser
1               5

<210> SEQ ID NO 22
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 22

Asp Ser Lys His His Ser Arg Asp His Leu Glu Ser Asp
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic Peptide
```

```
<400> SEQUENCE: 23

Asp Ser Lys His Lys Asp Arg Glu Tyr Val Phe Ser Asp
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 24

Asp Ser Lys His Phe His Arg Asp Phe Ile Tyr Ser Asp
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 25

Asp Ser Lys His Leu Ser Arg Glu Trp Met Trp Ser Asp
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 26

Asp Ser Lys His Trp Asp Arg Asp His Phe Glu Ser Asp
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 27

Asp Ser Lys His His His Arg Glu Tyr Leu Phe Ser Asp
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 28

Asp Ser Lys His Lys Ser Arg Asp Phe Val Tyr Ser Asp
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 29
```

Asp Ser Lys His Phe Asp Arg Glu Trp Ile Trp Ser Asp
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 30

Asp Ser Lys Lys Leu His Arg Asp His Met Glu Ser Asp
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 31

Asp Ser Lys Lys Trp Ser Arg Glu Tyr Phe Phe Ser Asp
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 32

Asp Ser Lys Lys His Asp Arg Asp Phe Leu Tyr Ser Asp
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 33

Asp Ser Lys Lys Lys His Arg Glu Trp Val Trp Ser Asp
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 34

Asp Ser Lys Lys Phe Ser Arg Asp His Ile Glu Ser Asp
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 35

Asp Ser His Lys Leu Asp Arg Glu Tyr Met Phe Ser Asp

<210> SEQ ID NO 36
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 36

Asp Ser His Lys Trp His Arg Asp Phe Phe Tyr Ser Asp
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 37

Asp Ser His Lys His Ser Arg Glu Trp Leu Trp Ser Asp
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 38

Asp Ser His His Lys Asp Arg Asp His Val Glu Ser Asp
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 39

Asp Ser His His Phe His Arg Glu Tyr Ile Phe Ser Asp
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 40

Asp Ser His His Leu Ser Arg Asp Phe Met Tyr Ser Asp
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 41

Asp Ser His His Trp Asp Arg Glu Trp Phe Trp Ser Asp
1               5                   10

```
<210> SEQ ID NO 42
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 42

Asp Ser His Lys His His Arg Asp His Leu Glu Ser Asp
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 43

Asp Ser His Lys Lys Ser Arg Glu Tyr Val Phe Ser Asp
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 44

Asp Ser His Lys Phe Asp Arg Asp Phe Ile Tyr Ser Asp
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 45

Asp Ser His Lys Leu His Arg Glu Trp Met Trp Ser Asp
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 46

Asp Ser His Lys Trp Ser Arg Asp His Phe Glu Ser Asp
1               5                   10

<210> SEQ ID NO 47
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 47

Phe Phe Asp Ser Lys His His Ser Arg Asp His Leu Glu Ser Asp
1               5                   10                  15

<210> SEQ ID NO 48
```

```
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 48

Phe Phe Asp Ser Lys His Lys Asp Arg Glu Tyr Val Phe Ser Asp
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 49

Phe Phe Asp Ser Lys His Phe His Arg Asp Phe Ile Tyr Ser Asp
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 50

Phe Phe Asp Ser Lys His Leu Ser Arg Glu Trp Met Trp Ser Asp
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 51

Phe Phe Asp Ser Lys His Trp Asp Arg Asp His Phe Glu Ser Asp
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 52

Phe Phe Asp Ser Lys His His His Arg Glu Tyr Leu Phe Ser Asp
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 53

Phe Phe Asp Ser Lys His Lys Ser Arg Asp Phe Val Tyr Ser Asp
1               5                   10                  15

<210> SEQ ID NO 54
<211> LENGTH: 15
<212> TYPE: PRT
```

<213> ORGANISM: Artificial Sequence
<220> FEATURE:
<223> OTHER INFORMATION: Synthetic Peptide

<400> SEQUENCE: 54

Phe Phe Asp Ser Lys His Phe Asp Arg Glu Trp Ile Trp Ser Asp
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 55

Phe Phe Asp Ser Lys Lys Leu His Arg Asp His Met Glu Ser Asp
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 56

Phe Phe Asp Ser Lys Lys Trp Ser Arg Glu Tyr Phe Phe Ser Asp
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 57

Phe Phe Asp Ser Lys Lys His Asp Arg Asp Phe Leu Tyr Ser Asp
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 58

Phe Phe Asp Ser Lys Lys Lys His Arg Glu Trp Val Trp Ser Asp
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 59

Phe Phe Asp Ser Lys Lys Phe Ser Arg Asp His Ile Glu Ser Asp
1               5                   10                  15

<210> SEQ ID NO 60
<211> LENGTH: 15
<212> TYPE: PRT
<213> ORGANISM: Artificial Sequence
<220> FEATURE:

<223> OTHER INFORMATION: Synthetic Peptide

<400> SEQUENCE: 60

Phe Phe Asp Ser His Lys Leu Asp Arg Glu Tyr Met Phe Ser Asp
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 61

Phe Phe Asp Ser His Lys Trp His Arg Asp Phe Phe Tyr Ser Asp
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 62

Phe Phe Asp Ser His Lys His Ser Arg Glu Trp Leu Trp Ser Asp
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 63

Phe Phe Asp Ser His His Lys Asp Arg Asp His Val Glu Ser Asp
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 64

Phe Phe Asp Ser His His Phe His Arg Glu Tyr Ile Phe Ser Asp
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 65

Phe Phe Asp Ser His His Leu Ser Arg Asp Phe Met Tyr Ser Asp
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic Peptide -continued

```
<400> SEQUENCE: 66

Phe Phe Asp Ser His His Trp Asp Arg Glu Trp Phe Trp Ser Asp
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 67

Phe Phe Asp Ser His Lys His His Arg Asp His Leu Glu Ser Asp
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 68

Phe Phe Asp Ser His Lys Lys Ser Arg Glu Tyr Val Phe Ser Asp
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 69

Phe Phe Asp Ser His Lys Phe Asp Arg Asp Phe Ile Tyr Ser Asp
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 70

Phe Phe Asp Ser His Lys Leu His Arg Glu Trp Met Trp Ser Asp
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 71

Phe Phe Asp Ser His Lys Trp Ser Arg Asp His Phe Glu Ser Asp
1               5                   10                  15

<210> SEQ ID NO 72
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 72
```

-continued

```
Asp Ser Lys Lys Phe Asp Arg Asp His Leu Tyr Ser Asp
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 73

Asp Ser Lys Trp Phe Asp Arg Asp His Leu Tyr Ser Asp
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 74

Asp Ser Asn Lys His His Arg Asp His Leu Tyr Ser Asp
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 75

Asp Ser Lys Trp His His Arg Asp His Leu Tyr Ser Asp
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 76

Asp Ser Asn Trp His His Arg Asp His Leu Tyr Ser Asp
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 77

Asp Ser Lys Lys His Asp Arg Asp His Leu Trp Ser Asp
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 78

Asp Ser Lys Lys His Asp Arg Asp His Leu Phe Ser Asp
1               5                   10
```

```
<210> SEQ ID NO 79
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 79

Asp Ser Lys Lys His Phe Arg Asp Lys Leu Tyr Ser Asp
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 80

Asp Ser Trp Trp His Lys Arg Asp Lys Leu Tyr Ser Asp
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 81

Asp Ser Lys Lys His Asp Arg Asp Lys Leu Phe Ser Asp
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 82

Asp Ser Lys Lys Phe His Arg Asp Phe Leu Tyr Ser Asp
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 83

Asp Ser Lys Lys Phe Lys Arg Asp Phe Leu Phe Ser Asp
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 84

Asp Ser Lys Lys Phe Asp Arg Asp Phe Leu Phe Ser Asp
1               5                   10
```

<210> SEQ ID NO 85
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 85

Asp Ser His Lys Phe Asp Arg Asp Phe Leu Tyr Ser Asp
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 86

Asp Ser Lys Lys Tyr Asp Arg Asp Phe Leu Trp Ser Asp
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 87

Asp Ser Lys Lys Phe Asp Arg Gly His Leu Tyr Ser Asp
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 88

Asp Ser Lys Trp His His Arg Gly His Leu Tyr Ser Asp
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 89

Asp Ser Lys Lys His Phe Arg Gly Lys Leu Tyr Ser Asp
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 90

Asp Ser Lys Lys Phe His Arg Gly Phe Leu Tyr Ser Asp
1               5                   10

<210> SEQ ID NO 91
<211> LENGTH: 13

```
<212> TYPE: PRT
<213> ORGANISM: Artificial Sequence
<220> FEATURE:
<223> OTHER INFORMATION: Synthetic Peptide

<400> SEQUENCE: 91

Asp Ser Lys Lys Tyr Asp Arg Gly Phe Leu Trp Ser Asp
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 92

Asp Ser Lys Trp Tyr His Arg Asn Lys Phe Trp Ser Asp
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 93

Asp Ser Gln Phe Ala His Arg Asn Ala Ser Ala Ser Asp
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 94

Asp Ser Trp Lys Ala Phe Arg Gly Ala Ser Ala Ser Asp
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 95

Asp Ser Gln Phe Ala Phe Arg Gly Ala Phe Trp Ser Asp
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 96

Asp Ser Met Cys Ala Phe Arg Gly Ala Lys Lys Ser Asp
1               5                   10

<210> SEQ ID NO 97
<211> LENGTH: 13
<212> TYPE: PRT
<213> ORGANISM: Artificial Sequence
```

```
<220> FEATURE:
<223> OTHER INFORMATION: Synthetic Peptide

<400> SEQUENCE: 97

Asp Ser Gln Phe Ala Phe Arg His Phe Ser Ala Ser Asp
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 98

Asp Ser Gln Trp Ala Phe Arg Gly Ala Phe Ala Ser Asp
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 99

Asp Ser Lys Phe Lys Phe Arg Tyr Ala Tyr Ala Ser Asp
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 100

Asp Ser Lys Phe His Phe Arg Tyr Ala Val Ala Ser Asp
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 101

Asp Ser Gln Phe Ala Tyr Arg Asn Ala Lys Ala Ser Asp
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 102

Asp Ser Gln Trp Ala Phe Arg His Ala Leu Phe Ser Asp
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Synthetic Peptide
```

```
<400> SEQUENCE: 103

Asp Ser Gln Trp Ala Phe Arg Asn Ala Phe Ala Ser Asp
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 104

Asp Ser Gln Phe Lys Phe Arg Gly Ala Phe Ala Ser Asp
1               5                   10

<210> SEQ ID NO 105
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 105

Asp Ser Gln Cys Leu Phe Arg Gly Ala Phe Ala Ser Asp
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 106

Asp Ser Lys Phe Ala Phe Arg Gly Gly Ile Ala Ser Asp
1               5                   10

<210> SEQ ID NO 107
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Xaa stands for ornithine fluoroamidine

<400> SEQUENCE: 107

Phe Phe Asp Ser Lys His Phe Asp Xaa Glu Trp Ile Trp Ser Asp
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Xaa stands for ornithine fluoroamidine

<400> SEQUENCE: 108

Phe Phe Asp Ser His Lys Trp His Xaa Asp Phe Phe Tyr Ser Asp
1               5                   10                  15
```

```
<210> SEQ ID NO 109
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Xaa stands ornithine fluoroamidine

<400> SEQUENCE: 109

Phe Phe Asp Ser His Lys Phe Asp Xaa Asp Phe Ile Tyr Ser Asp
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Xaa stands for ornithine fluoroamidine

<400> SEQUENCE: 110

Phe Phe Asp Ser His Lys Leu His Xaa Glu Trp Met Trp Ser Asp
1               5                   10                  15

<210> SEQ ID NO 111
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa stands for ornithine fluoroamidine

<400> SEQUENCE: 111

Asp Ser His Lys Phe Asp Xaa Asp Phe Ile Tyr Ser Asp
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: X stands for ornithin fluoroamidine
<220> FEATURE:
<221> NAME/KEY: MISC_FEATURE
<222> LOCATION: (7)..(7)
<223> OTHER INFORMATION: Xaa stands for ornithine fluoroamidine

<400> SEQUENCE: 112

Asp Ser Lys Lys His Asp Xaa Asp Phe Leu Tyr Ser Asp
1               5                   10

<210> SEQ ID NO 113
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<222> LOCATION: (9)..(9)
<223> OTHER INFORMATION: Xaa stands for ornithine chloroamidine

<400> SEQUENCE: 113

Phe Phe Asp Ser Lys His Phe Asp Xaa Glu Trp Ile Trp Ser Asp
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Xaa stands for ornithine chloroamidine

<400> SEQUENCE: 114

Phe Phe Asp Ser His Lys Trp His Xaa Asp Phe Phe Tyr Ser Asp
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Xaa stands for ornithine chloroamidine

<400> SEQUENCE: 115

Phe Phe Asp Ser His Lys Phe Asp Xaa Asp Phe Ile Tyr Ser Asp
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Xaa stands for ornithine chloroamidine

<400> SEQUENCE: 116

Phe Phe Asp Ser His Lys Leu His Xaa Glu Trp Met Trp Ser Asp
1               5                   10                  15

<210> SEQ ID NO 117
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa stands for ornithine chloroamidine

<400> SEQUENCE: 117

Asp Ser His Lys Phe Asp Xaa Asp Phe Ile Tyr Ser Asp
1               5                   10

<210> SEQ ID NO 118
<211> LENGTH: 13
<212> TYPE: PRT
```

<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa stands for ornithine chloroamidine

<400> SEQUENCE: 118

Asp Ser Lys Lys His Asp Xaa Asp Phe Leu Tyr Ser Asp
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 119

His Phe Asp Xaa Glu Trp Ile
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 120

Lys Trp His Xaa Asp Phe Phe
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 121

Lys Leu His Xaa Glu Trp Met
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 122

Lys Phe Asp Xaa Asp Phe Ile
1               5

```
<210> SEQ ID NO 123
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 123

Lys His Asp Xaa Asp Phe Leu
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 124

Lys Phe Asp Xaa Asp Phe Ile
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 125

Lys Trp His Xaa Asp Phe Phe
1               5

<210> SEQ ID NO 126
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for ornithine fluoroamidine

<400> SEQUENCE: 126

Thr Asp Xaa Gly Ser
1               5

<210> SEQ ID NO 127
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for ornithine chloroamidine
```

```
<400> SEQUENCE: 127

Gly Asp Xaa Gly Ser
1               5

<210> SEQ ID NO 128
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for ornithine chloroamidine

<400> SEQUENCE: 128

Tyr Asp Xaa Gly Ser
1               5

<210> SEQ ID NO 129
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for ornithine fluoroamidine

<400> SEQUENCE: 129

Phe Asp Xaa Asp Phe
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine
<220> FEATURE:
<221> NAME/KEY: MISC_FEATURE
<222> LOCATION: (8)..(8)
<223> OTHER INFORMATION: Xaa stands for AEEAc

<400> SEQUENCE: 130

Lys Phe Asp Xaa Asp Phe Ile Xaa
1               5

<210> SEQ ID NO 131
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine
<220> FEATURE:
<221> NAME/KEY: MISC_FEATURE
<222> LOCATION: (8)..(8)
<223> OTHER INFORMATION: Xaa stands for AEEAc

<400> SEQUENCE: 131

Lys Phe Asp Xaa Asp Phe Ile Xaa
```

```
<210> SEQ ID NO 132
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 132

Lys Phe Asp Xaa Asp Phe Ile
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine
<220> FEATURE:
<221> NAME/KEY: MISC_FEATURE
<222> LOCATION: (8)..(8)
<223> OTHER INFORMATION: Xaa stands for AEEAc

<400> SEQUENCE: 133

Lys Trp His Xaa Asp Phe Phe Xaa
1               5

<210> SEQ ID NO 134
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine
<220> FEATURE:
<221> NAME/KEY: MISC_FEATURE
<222> LOCATION: (8)..(8)
<223> OTHER INFORMATION: Xaa stands for AEEAc

<400> SEQUENCE: 134

Lys Trp His Xaa Asp Phe Phe Xaa
1               5

<210> SEQ ID NO 135
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 135

Lys Trp His Xaa Asp Phe Phe
1               5

<210> SEQ ID NO 136
```

```
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 136

Lys Phe Asp Xaa Asp Phe Ile
1               5

<210> SEQ ID NO 137
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 137

Lys Phe Asp Xaa Asp Phe Ile Tyr
1               5

<210> SEQ ID NO 138
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 138

Lys Phe Asp Xaa Asp Phe Ile Lys
1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 139

Lys Trp His Xaa Asp Phe Phe
1               5

<210> SEQ ID NO 140
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 140
```

```
Lys Trp His Xaa Asp Phe Phe Tyr
1               5
```

<210> SEQ ID NO 141
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa stands for ornithine fluoroamidine

<400> SEQUENCE: 141

```
Lys Trp His Xaa Asp Phe Phe Lys
1               5
```

<210> SEQ ID NO 142
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for ornithine chloroamidine

<400> SEQUENCE: 142

```
Gly Asp Xaa Gly Ser
1               5
```

<210> SEQ ID NO 143
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa stands for ornithine chloroamidine

<400> SEQUENCE: 143

```
Tyr Asp Xaa Gly Ser
1               5
```

<210> SEQ ID NO 144
<211> LENGTH: 13
<212> TYPE: PRT
<213> ORGANISM: Artificial Sequence Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: Citrullinated Arginine

<400> SEQUENCE: 144

```
Asp Ser Lys Lys Phe His Arg Gly Phe Leu Tyr Ser Asp
1               5                   10
```

<210> SEQ ID NO 145
<211> LENGTH: 4
<212> TYPE: PRT
<213> ORGANISM: Artificial Sequence -continued

```
<220> FEATURE:
<223> OTHER INFORMATION: Synthetic Peptide

<400> SEQUENCE: 145

Asp Glu Val Asp
1
```